United States Patent
Zhou et al.

(10) Patent No.: US 8,841,443 B2
(45) Date of Patent: Sep. 23, 2014

(54) SILAFLUORENE METALLOPORPHYRIN-BENZENE ORGANIC SEMICONDUCTOR MATERIAL AND PREPARING METHOD AND USES THEREOF

(75) Inventors: Mingjie Zhou, Shenzhen (CN); Jie Huang, Shenzhen (CN); Yijin Liu, Shenzhen (CN)

(73) Assignee: Ocean's King Lighting & Science Technology Co., Ltd., Shenzhen, Guangdong (CN)

( * ) Notice: Subject to any disclaimer, the term of this patent is extended or adjusted under 35 U.S.C. 154(b) by 0 days.

(21) Appl. No.: 13/821,523

(22) PCT Filed: Sep. 13, 2010

(86) PCT No.: PCT/CN2010/076847
§ 371 (c)(1),
(2), (4) Date: Mar. 7, 2013

(87) PCT Pub. No.: WO2012/034267
PCT Pub. Date: Mar. 22, 2012

(65) Prior Publication Data
US 2013/0165646 A1   Jun. 27, 2013

(51) Int. Cl.
*C07D 487/22* (2006.01)
*C07F 1/08* (2006.01)
(Continued)

(52) U.S. Cl.
CPC ............... *C07F 7/0816* (2013.01); *C07F 1/08* (2013.01); *C07D 487/22* (2013.01); *H01L 51/424* (2013.01); *H01L 51/0037* (2013.01); *H01L 51/0092* (2013.01); *C08G 2261/37* (2013.01); *C08G 2261/3221* (2013.01); *C07F 15/065* (2013.01); *Y02E 10/549* (2013.01); *C08G 2261/312* (2013.01); *C07F 7/2284* (2013.01); *H01L 51/009* (2013.01); *H01L 51/0047* (2013.01); *C08G 2261/3244* (2013.01); *C08G 61/124* (2013.01); *H01L 51/0043* (2013.01); *H01L 51/0036* (2013.01); *H01L 51/5016* (2013.01); *H01L 51/0094* (2013.01); *H01L 51/0091* (2013.01); *C07F 3/06* (2013.01); *C08G 2261/411* (2013.01); *C08G 2261/124* (2013.01); *C08G 2261/148* (2013.01); *C08G 2261/51* (2013.01); *C08G 2261/91* (2013.01); *H01L 51/0083* (2013.01); *C07F 15/025* (2013.01); *C07F 3/08* (2013.01); *C08G 2261/144* (2013.01)
USPC .......................................................... 540/145

(58) Field of Classification Search
CPC ...................................................... C07F 7/0816
USPC ........................................................ 540/145
See application file for complete search history.

(56) References Cited

U.S. PATENT DOCUMENTS

2010/0177264 A1   7/2010   Tsubomura et al.

FOREIGN PATENT DOCUMENTS

EP          2551271 A1     1/2013
JP       2000-095870 A     4/2000
(Continued)

OTHER PUBLICATIONS

Binsong Li, et al., Porphyrins with Four Monodisperse Oligofluorene Arms as Efficient Red Ligh-Emitting Materials, J. Am. Chem Soc. 2004, 126, 3430-3431.

*Primary Examiner* — Brian McDowell
(74) *Attorney, Agent, or Firm* — Shimokaji & Associates P.C.

(57) ABSTRACT

A silafluorene metalloporphyrin- benzene organic semiconductor material and preparing method and uses thereof are provided. The structure of the silafluorene metalloporphyrin-benzene organic semiconductor material is defined by structure formula (I):

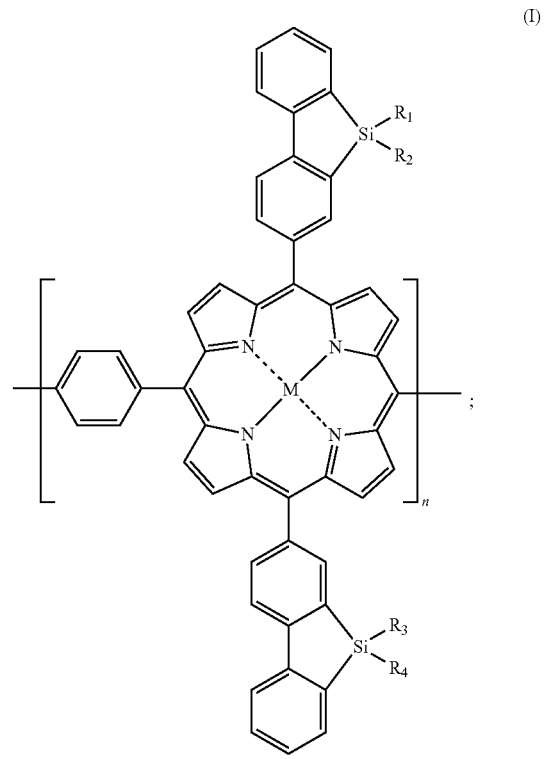

wherein: n is an integer between 1 and 100, $R_1, R_2, R_3, R_4$ are H, alkyl with $C_1$-$C_{32}$, phenyl, alkyl benzene or alkoxyl benzene containing one or more $C_1$-$C_{32}$, M is a metal ion. The silafluorene metalloporphyrin- benzene organic semiconductor material has good solubility, high carrier mobility, strong absorbance, wide absorbent range to light and elevated utilization ratio of solar light. Besides, the process of the preparing method is simple and easy to operate and control.

9 Claims, 2 Drawing Sheets

(51) Int. Cl.
| | | |
|---|---|---|
| C07F 7/08 | (2006.01) | |
| C07F 15/06 | (2006.01) | |
| C07F 7/22 | (2006.01) | |
| C08G 61/12 | (2006.01) | |
| C07F 3/06 | (2006.01) | |
| C07F 15/02 | (2006.01) | |
| C07F 3/08 | (2006.01) | |
| H01L 51/42 | (2006.01) | |
| H01L 51/00 | (2006.01) | |
| H01L 51/50 | (2006.01) | |

(56) References Cited

FOREIGN PATENT DOCUMENTS

| | | |
|---|---|---|
| JP | 2002-515001 A | 5/2002 |
| JP | 2013-518151 A | 5/2013 |
| JP | 2013-531093 A | 8/2013 |
| JP | 2013-532190 A | 8/2013 |

SILAFLUORENE METALLOPORPHYRIN-BENZENE ORGANIC SEMICONDUCTOR MATERIAL AND PREPARING METHOD AND USES THEREOF

FIELD OF THE INVENTION

The present invention relates to an organic semiconductor material, particularly relates to a silafluorenyl metalloporphyrin-benzene organic semiconductor material.

The present invention also relates to preparing method of silafluorenyl metalloporphyrin-benzene organic semiconductor material and uses thereof.

BACKGROUND OF THE INVENTION

A persistent difficulty and hotspot in the field of photovoltaics is to prepare low-cost, high-energy solar cells using cheap materials. Currently, the application of crystalline silicon cell used for the ground is greatly confined because of its complicated process and high cost. In order to reduce the cost of the battery, it has been a long time for people to seek for a new solar cell material to cut the cost and expand the application. Organic semiconductor material has attracted considerable attention owing to its advantages of available raw material, low cost, simple process, good environmental stability and good photovoltaic effect. Since photo-induced electron transfer phenomenon between conjugated polymer and $C_{60}$ was reported on Science (N. S Sariciftci, L. S milowitz, A. J. Heeger, et al. Science, 1992, 258, 1474) by N. S. Sariciftci, et al. in 1992, considerable efforts have been directed toward developing polymer solar cells, and a rapid development is achieved. However, the conversion efficiency is much lower than that of inorganic solar cells. What mainly constrain performance improvements are: mismatch between spectral response of organic semiconductor material and solar spectrum, relatively lower carrier mobility of organic semiconductor, relatively lower efficiency of electron collecting of carrier, etc. To put polymer solar cell into practice, a primary task in such field is to develop new material and to substantially promote its energy conversion efficiency.

Porphyrin is the collective name for types of macrocyclic compounds of substituted porphins, porphin consisting of four pyrrole rings joined together by four methine groups is delocalized π-electrons conjugated system of a flat macrocycle structure having alternating single and double bonds. They have good quantum efficiency in charge-transfer and energy-transfer reaction, great electronic buffer properties, photoelectric magnetic properties, stiffness, as well as excellent thermal stability and environmental stability. Thus, porphyrins organic semiconductor materials are a kind of promising materials, of which the application in the field of photovoltaic is widely investigated. Almost all of the elements and some nonmetals in the Periodic Table can react with porphyrins to form coordination complex. These compounds include most of the metals in main groups and subgroups, some lanthanide metals (Pr, Eu, and Yb etc.) have been synthesized. Porphyrins are macro conjugated system with 18 of π-electrons, so the mobility of electrons migrating within the ring is pretty good, as a consequence, most metalloporphyrin have good photoelectric properties.

However, metalloporphyrin-benzene organic semiconductor material containing silafluorenyl has not been reported on any literature and patent, which greatly refined the application of organic semiconductor material. Thus, the present invention developed a kind of silafluorenyl metalloporphyrin-benzene organic semiconductor material. By the introduction of silafluorene group into parent porphyrin, coordination of metal ions, adjustment of band gaps of porphyrin copolymer, the present invention gains better stability, film forming property, and broadens the absorption range of visible spectrum to near-infrared region, and improves the use of sunlight, at the same time, carrier mobility is improved, the application in the field of organic solar cells and others is broadened.

SUMMARY OF THE INVENTION

The present invention aims to provide a silafluorenyl metalloporphyrin-benzene organic semiconductor material, solving the foregoing problems.

The present invention also aims to provide preparing method of a silafluorenyl metalloporphyrin-benzene organic semiconductor material and uses thereof.

The silafluorenyl metalloporphyrin-benzene organic semiconductor material involved in the present invention has following structure formula (I):

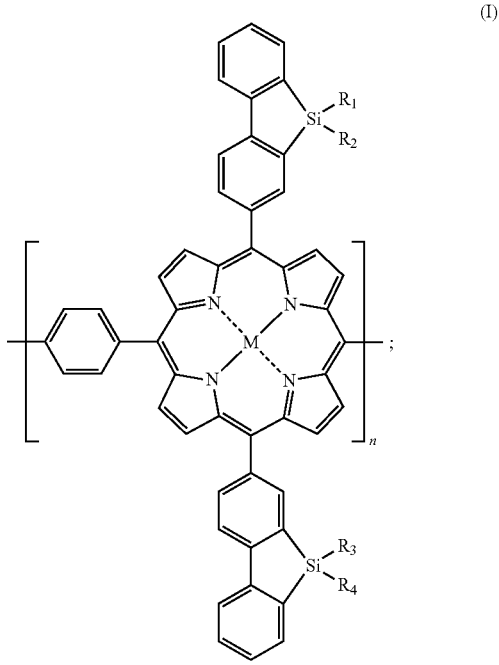

(I)

where n is an integer between 1 and 100, $R_1$, $R_2$, $R_3$, $R_4$ are identical or different H, alkyl with $C_1$-$C_{32}$, phenyl, alkyl phenyl or alkoxyl phenyl containing one or more identical or different $C_1$-$C_{32}$; M is metal ion, which can be but not limited to $Zn^{2+}$, $Cu^{2+}$, $Fe^{2+}$, $Co^{2+}$, $Cd^{2+}$, $Pt^{2+}$, $Zr^{2+}$, $Mn^{2+}$, $Ni^{2+}$, $Pb^{2+}$, $Sn^{2+}$ and other metal ions.

The preparing method of silafluorenyl metalloporphyrin-benzene organic semiconductor material designed by the present invention comprises the following steps:

step S1, in the presence of oxidant and the first catalyst, dissolving dipyrromethane having the structure formula of

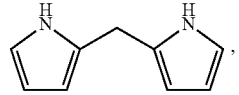 [SMILES: c1c[nH]c(Cc2ccc[nH]2)c1]

the first silafluorene derivative having the structure formula of

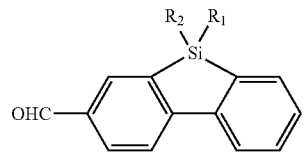

and the second silafluorene derivative having the structure formula of

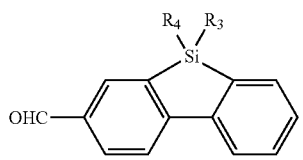

in the first organic solvent, reacting at the temperature of 20° C. to 100° C. for 1 h to 24 h to obtain silafluorenyl porphyrin derivative having the structure formula of

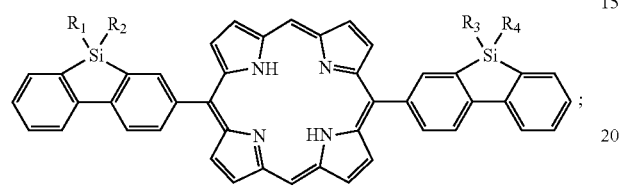

wherein, $R_1$, $R_2$, $R_3$, $R_4$ are H, alkyl with $C_1$-$C_{32}$, phenyl, alkyl phenyl or alkoxyl phenyl containing one or more $C_1$-$C_{32}$, respectively; the chemical equation is:

step S2, adding the silafluorenyl porphyrin derivative obtained from step S1 and brominating agent into the second organic solvent, reacting at the temperature of 0° C. to 120° C. for 1 h to 72 h to obtain dibromo-silafluorenyl porphyrin derivative having the structure formula of

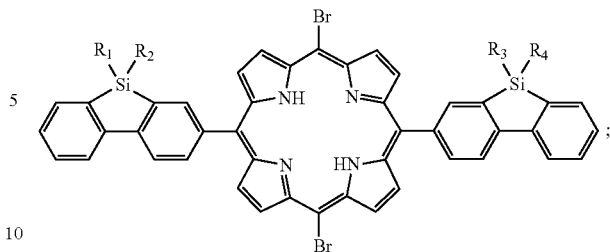

the chemical equation is:

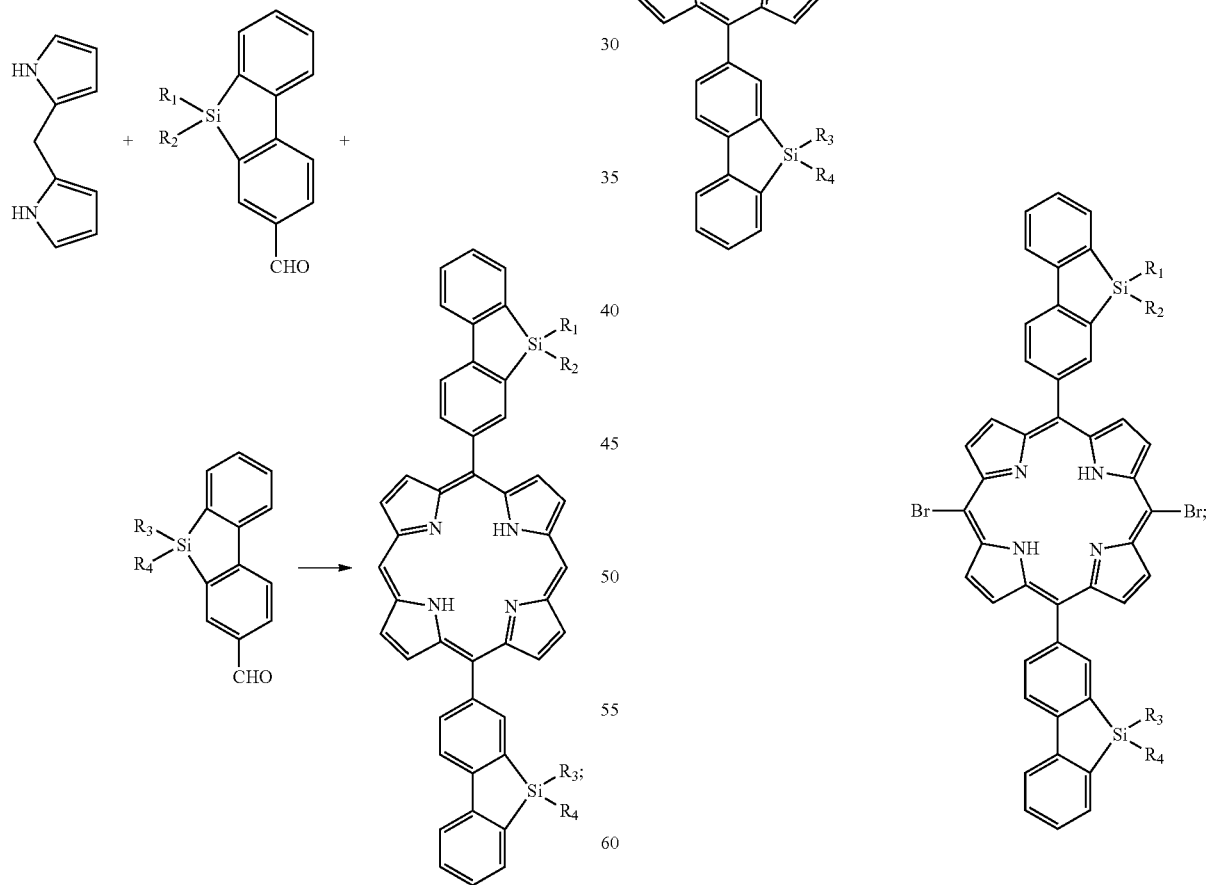

step S3, dissolving the dibromo-silafluorenyl porphyrin derivative obtained from step S2 in the third organic solvent, then adding solution containing M metal ion, stirring at the temperature of 0° C. to 30° C. for 0.5 h to 24 h to obtain dibromo-silafluorenyl metalloporphyrin derivative having the structure formula of

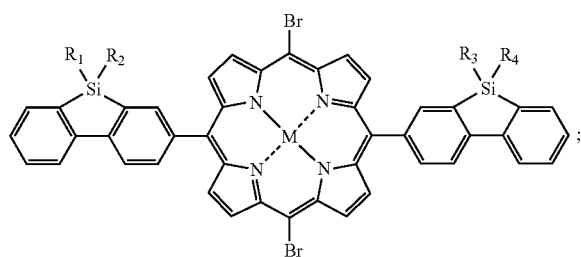

the chemical equation is:

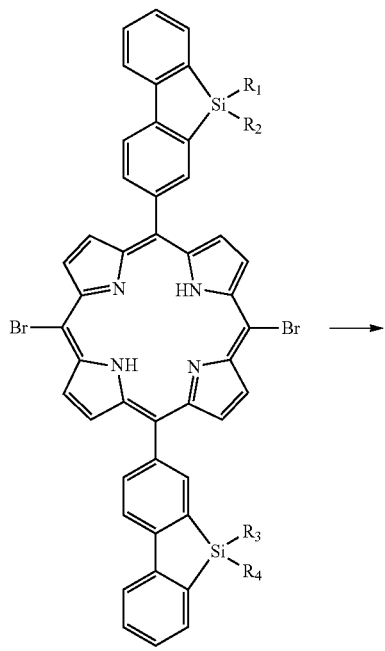

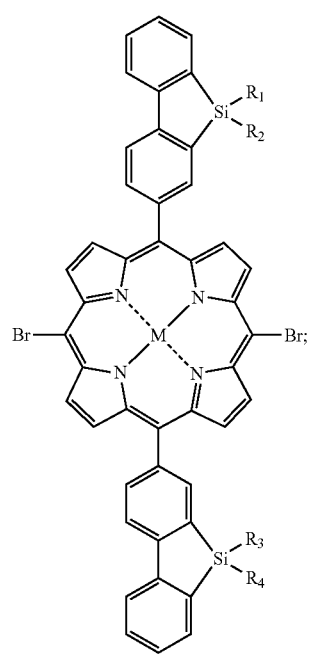

step S4, in the oxygen-free environment, in the presence of the second catalyst and the fourth organic solvent, dibromo-silafluorenyl metalloporphyrin derivative obtained from step S3 and 1,4-p-bis(4,4,5,5-tetramethyl-1,3,2-dioxaborolan) benzene having the structure formula of

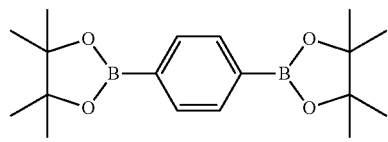

were carried out the Suzuki coupling reaction according to the molar ratio of 1:2 to 2:1, at 50° C. to 120° C. for 12 h to 72 h to obtain said silafluorenyl metalloporphyrin-benzene organic semiconductor material having the structure formula of

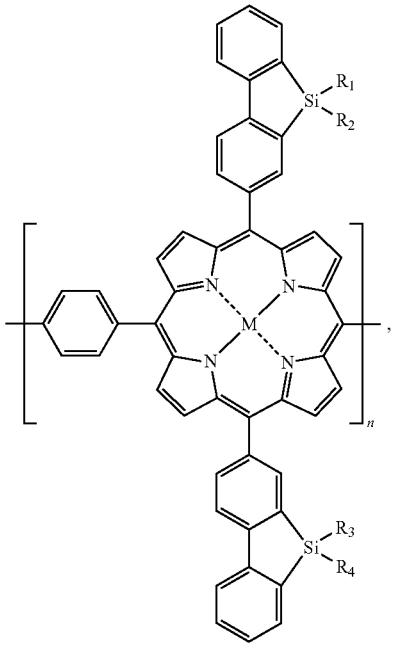

where n is an integer between 1 and 100; the chemical equation is:

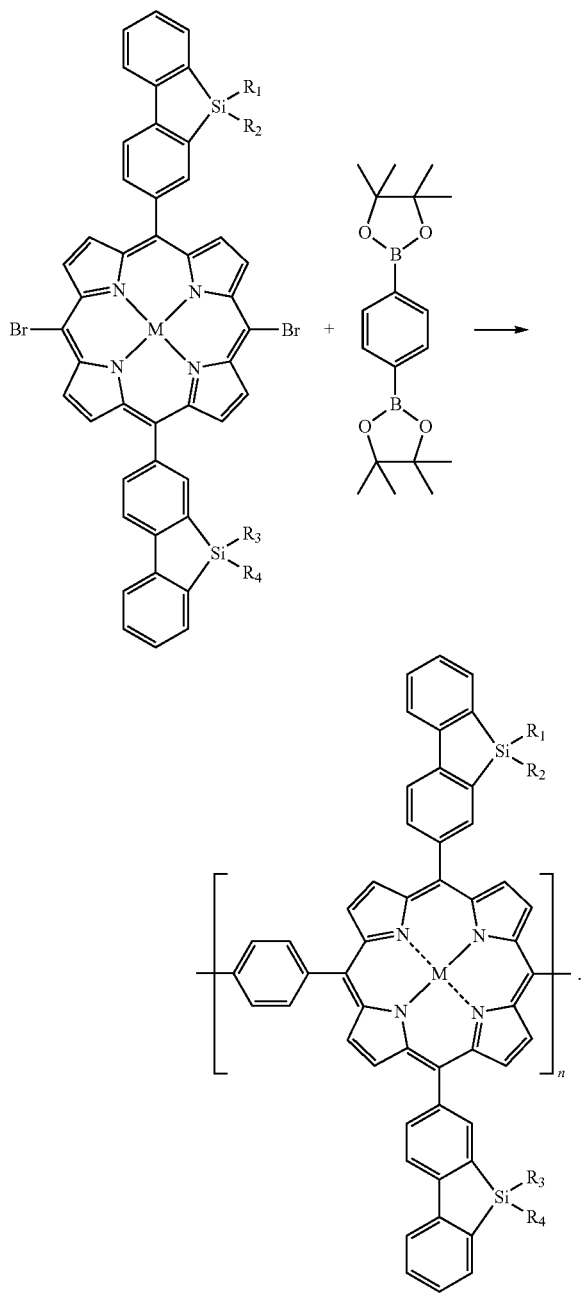

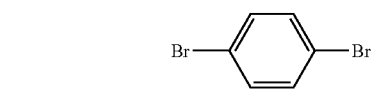

In said preparing method of silafluorenyl metalloporphyrin-benzene organic semiconductor material, preferably:

in said step S1, the molar ratio of dipyrromethane, the first silafluorene derivative and the second silafluorene derivative is a:(b+c)=1:1, where a≥b>0, and c≥0; said the first catalyst is propionic acid, trifluoroacetic acid; said oxidant is 2,3-dichloro-5,6-dicyano-1,4-benzoquinone; said the first organic solvent is one or two of trichloromethane and dichloromethane;

in said step S2, the molar ratio of used said silafluorenyl porphyrin derivative to used said brominating agent is in the range of 1:2 to 1:5; said brominating agent is N-bromobutanimide; said the second organic solvent is at least one of tetrahydrofuran, chloroform, dimethylformamide and orthodichlorobenzene;

in said step S3, the molar ratio of said dibromo-silafluorenyl metalloporphyrin derivative to M metal ion is in the range of 1:1 to 1:5; said the third organic solvent is at least one of trichloromethane, tetrahydrofuran, benzene, methylbenzene and dichloromethane; in said solution containing M metal ion, M metal ion is one of $Zn^{2+}$, $Cu^{2+}$, $Fe^{2+}$, $Co^{2+}$, $Cd^{2+}$, $Pt^{2+}$, $Zr^{2+}$, $Mn^{2+}$, $Ni^{2+}$, $Pb^{2+}$ and $Sn^{2+}$, solvent is at least one of methanol, ethanol and water;

in said step S4, said the second catalyst is organopalladium or mixture of organopalladium and organic phosphine ligand;

said organopalladium is $Pd_2(dba)_3$, $Pd(PPh_3)_4$, $Pd(OAc)_2$ or $Pd(PPh_3)_2Cl_2$;

said organic phosphine ligand is $P(o\text{-}Tol)_3$ or tricyclohexyl phosphine;

said the fourth organic solvent is at least one of tetrahydrofuran, dichloromethane, chloroform, dioxane, dimethylformamide, glycol dimethyl ether, dimethyl sulfoxide, benzene, chlorobenzene and methylbenzene;

in addition, step S4 further comprises preparation of 1,4-p-bis(4,4,5,5-tetramethyl-1,3,2-dioxaborolan)benzene comprising:

adding p-dibromobenzene having the structure formula of

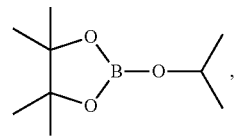

into the fifth organic solvent, cooling to −78° C. with liquid nitrogen/isopropanol, then dripping n-butyl lithium (n-BuLi, similarly hereinafter) and reacting at −78° C. for 1 h to 3 h, after that, adding 2-isopropoxy-4,4,5,5-tetramethyl-1,3,2-dioxaborolane having the structure formula of continue to react at −78° C. for 0.5 h to 2 h, then warming naturally to room temperature and reacting for 6 h to 36 h to obtain said 1,4-p-bis(4,4,5,5-tetramethyl-1,3,2-dioxaborolan)benzene; where, said the fifth organic solution is at least one of tetrahydrofuran, diethyl ether and dioxane; the molar ratio of said p-dibromobenzene to 2-isopropoxy-4,4,5,5-tetramethyl-1,3,2-dioxaborolane is in the range of 1:2~5; the chemical equation is:

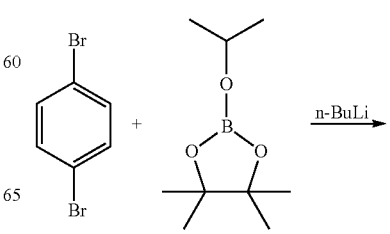

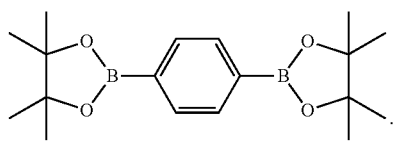

Uses of said silafluorenyl metalloporphyrin-benzene organic semiconductor material in the field of organic solar cells, organic light-emitting devices, organic field effect transistors, organic optical storages, organic nonlinear devices, organic laser devices and others.

Compared to the prior art, the present invention has the following advantages:

1. the silafluorene unit involved in the organic semiconductor material of the present invention has great thermal stability, high electron affinity and good capacity of electron injecting and transporting;

2. the organic semiconductor material of the present invention also contains porphyrin unit which is delocalized π-electrons conjugated system of a flat macrocycle structure, they have good quantum efficiency in charge-transfer and energy-transfer reaction, great electronic buffer properties, photoelectric magnetic properties, stiffness, as well as excellent thermal stability and environmental stability;

3. the organic semiconductor material of the present invention contains both silafluorene structure unit and porphyrin unit, possessing their performance advantages, broadening the absorption range of said organic semiconductor material to sunlight, achieving a better match with solar spectrum, thus the uses of said organic semiconductor material in the field of polymer solar cells, organic light emitting devices, organic field effect transistors, organic optical storages or/and organic laser devices are broadened;

4. preparing method of said organic semiconductor material is simple, easy to operate and control.

DETAILED DESCRIPTION OF ILLUSTRATED EMBODIMENTS

Figure 1:
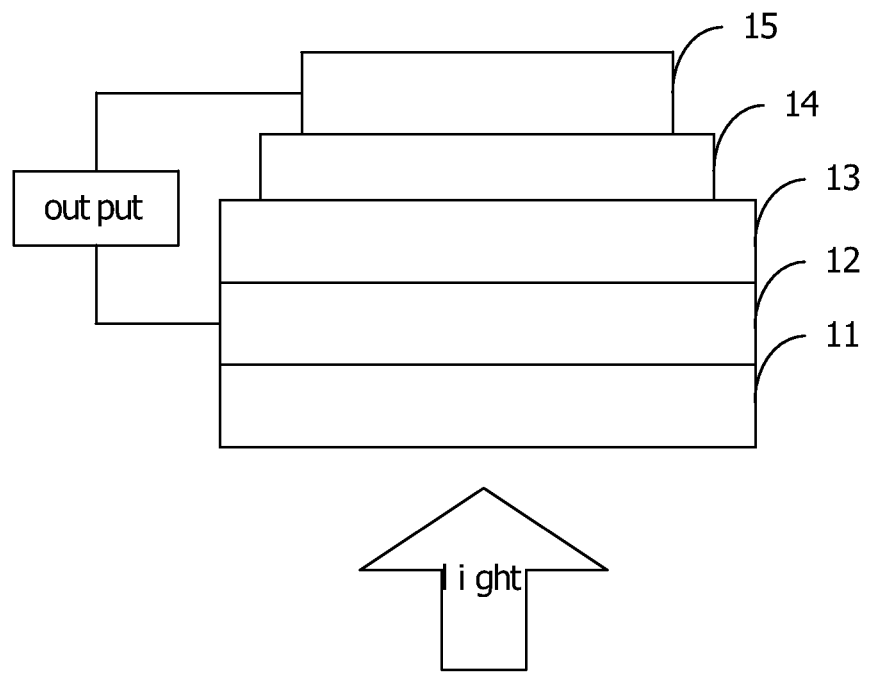
FIG. 1 is a structure diagram of organic solar cell device using organic semiconductor material of the present invention as active layer.

The silafluorenyl metalloporphyrin-benzene organic semiconductor material involved in the present invention has following structure formula (I):

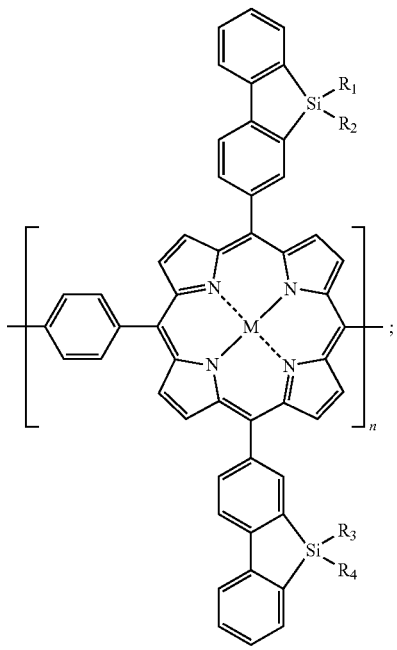

where n is an integer between 1 and 100, $R_1$, $R_2$, $R_3$, $R_4$ are identical or different H, alkyl with $C_1$-$C_{32}$, phenyl, alkyl phenyl or alkoxyl phenyl containing one or more identical or different $C_1$-$C_{32}$, respectively; M is metal ion, which can be but not limited to $Zn^{2+}$, $Cu^{2+}$, $Fe^{2+}$, $Co^{2+}$, $Cd^{2+}$, $Pt^{2+}$, $Zr^{2+}$, $Mn^{2+}$, $Ni^{2+}$, $Pb^{2+}$, $Sn^{2+}$ and other metal ions.

The preparing method of silafluorenyl metalloporphyrin-benzene organic semiconductor material designed by the present invention comprises the following steps:

step S1, in the presence of oxidant and the first catalyst, dissolving dipyrromethane having the structure formula of

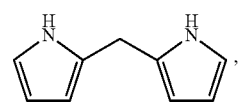 [SMILES: c1c[nH]c(Cc2ccc[nH]2)c1]

the first silafluorene derivative having the structure formula of

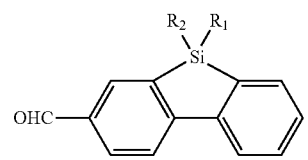

and the second silafluorene derivative having the structure formula of

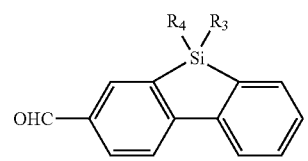

in the first organic solvent, reacting at the temperature of 20° C. to 100° C. for 1 h to 24 h to obtain silafluorenyl porphyrin derivative having the structure formula of

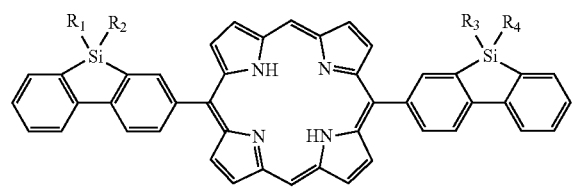

where $R_1$, $R_2$, $R_3$, $R_4$ are H, alkyl with $C_1$-$C_{32}$, phenyl, alkyl phenyl or alkoxyl phenyl containing one or more $C_1$-$C_{32}$, respectively; the chemical equation is:

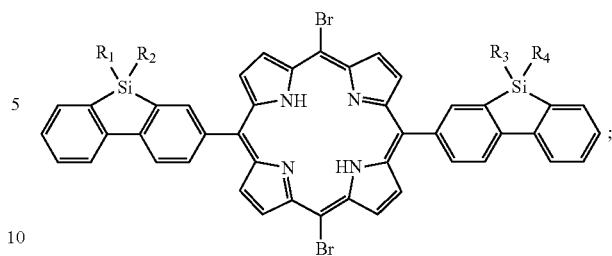

the chemical equation is:

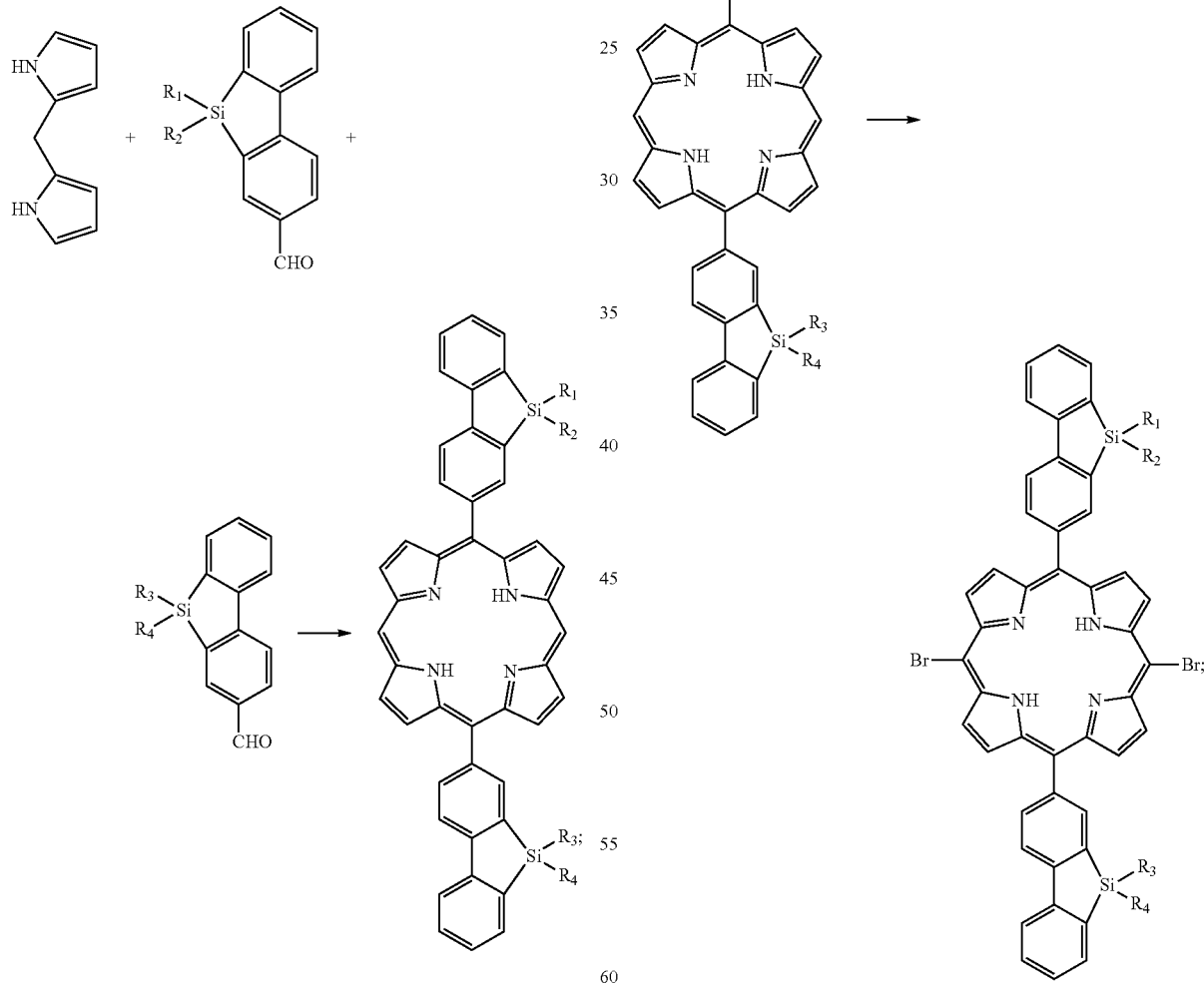

step S2, adding the silafluorenyl porphyrin derivative obtained from step S1 and brominating agent into the second organic solvent, reacting at the temperature of 0° C. to 120° C. for 1 h to 72 h to obtain dibromo-silafluorenyl porphyrin derivative having the structure formula of step S3, dissolving the dibromo-silafluorenyl porphyrin derivative obtained from step S2 in the third organic solvent, then adding solution containing M metal ion, stirring at the temperature of 0° C. to 30° C. for 0.5 h to 24 h to obtain dibromo-silafluorenyl metalloporphyrin derivative having the structure formula of

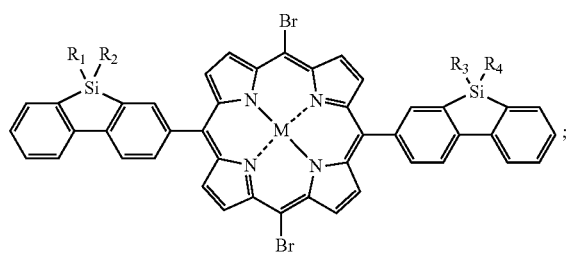

the chemical equation is:

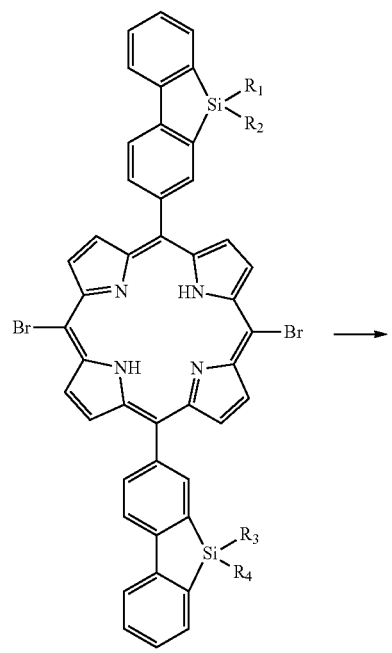

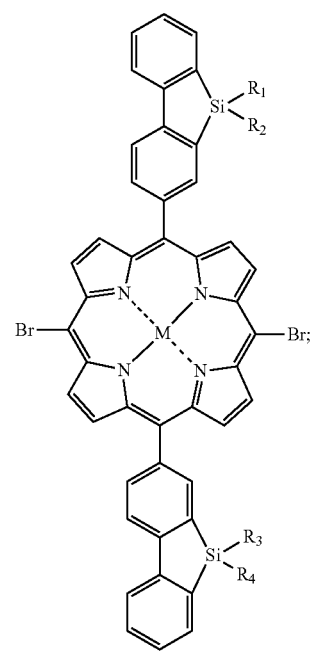

step S4, in the oxygen-free environment, in the presence of the second catalyst and the fourth organic solvent, dibromo-silafluorenyl metalloporphyrin derivative obtained from step S3 and 1,4-p-bis(4,4,5,5-tetramethyl-1,3,2-dioxaborolan) benzene having the structure formula of

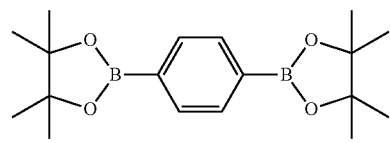

were carried out the Suzuki coupling reaction according to the molar ratio of 1:2 to 2:1, at 50° C. to 120° C. for 12 h to 72 h to obtain said silafluorenyl metalloporphyrin-benzene organic semiconductor material having the structure formula of

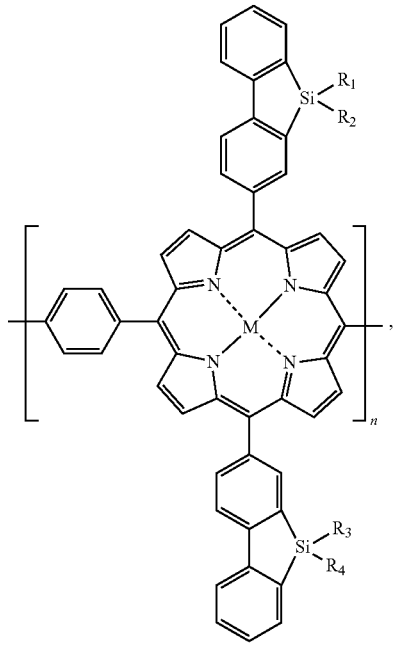

where n is an integer between 1 and 100; the chemical equation is:

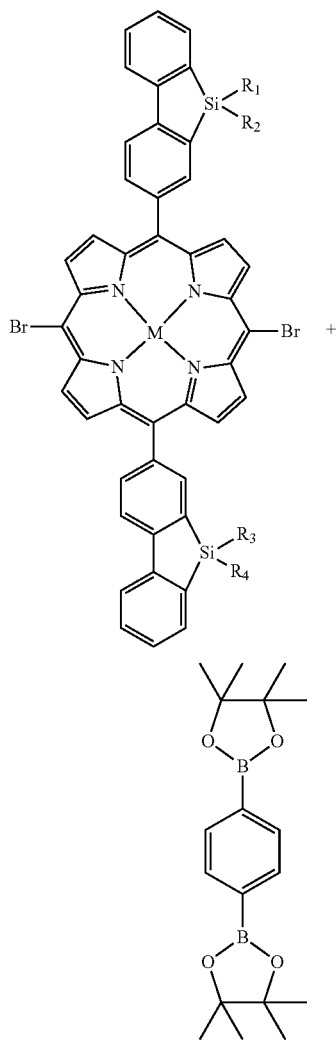

In said preparing method of silafluorenyl metalloporphyrin-benzene organic semiconductor material, preferably:

in said step S1, the molar ratio of dipyrromethane, the first silafluorene derivative and the second silafluorene derivative is a:(b+c)=1:1, where a≥b>0, and c≥0; said the first catalyst is propionic acid, trifluoroacetic acid; said oxidant is 2,3-dichloro-5,6-dicyano-1,4-benzoquinone; said the first organic solvent is one or two of trichloromethane and dichloromethane;

in said step S2, the molar ratio of used said silafluorenyl porphyrin derivative to used said brominating agent is in the range of 1:2 to 1:5; said brominating agent is N-bromobutanimide; said the second organic solvent is at least one of tetrahydrofuran, chloroform, dimethylformamide and orthodichlorobenzene;

in said step S3, the molar ratio of said dibromo-silafluorenyl metalloporphyrin derivative to M metal ion is in the range of 1:1 to 1:5; said the third organic solvent is at least one of trichloromethane, tetrahydrofuran, benzene, methylbenzene and dichloromethane; in said solution containing M metal ion, M metal ion is one of $Zn^{2+}$, $Cu^{2+}$, $Fe^{2+}$, $Co^{2+}$, $Cd^{2+}$, $Pt^{2+}$, $Zr^{2+}$, $Mn^{2+}$, $Ni^{2+}$, $Pb^{2+}$ and $Sn^{2+}$, solvent is at least one of methanol, ethanol and water;

in said step S4, said the second catalyst is organopalladium or mixture of organopalladium and organic phosphine ligand;

said organopalladium is $Pd_2(dba)_3$, $Pd(PPh_3)_4$, $Pd(OAc)_2$ or $Pd(PPh_3)_2Cl_2$;

said organic phosphine ligand is $P(o\text{-}Tol)_3$ or tricyclohexyl phosphine;

said the fourth organic solvent is at least one of tetrahydrofuran, dichloromethane, chloroform, dioxane, dimethylformamide, glycol dimethyl ether, dimethyl sulfoxide, benzene, chlorobenzene and methylbenzene;

in addition, step S4 further comprises preparation of 1,4-p-bis(4,4,5,5-tetramethyl-1,3,2-dioxaborolan)benzene comprising:

adding p-dibromobenzene having the structure formula of into the fifth organic solvent, cooling to −78° C. with liquid nitrogen/isopropanol, then dripping n-butyl lithium (n-BuLi) and reacting at −78° C. for 1 h to 3 h, after that, adding 2-isopropoxy-4,4,5,5-tetramethyl-1,3,2-dioxaborolane having the structure formula of continue to react at −78° C. for 0.5 h to 2 h, then warming naturally to room temperature and reacting for 6 h to 36 h to obtain said 1,4-p-bis(4,4,5,5-tetramethyl-1,3,2-dioxaborolan)benzene; where, said the fifth organic solution is at least one of tetrahydrofuran, diethyl ether and dioxane; the molar ratio of said p-dibromobenzene to 2-isopropoxy-4,4,5,5-tetramethyl-1,3,2-dioxaborolane is in the range of 1:2-5; the chemical equation is:

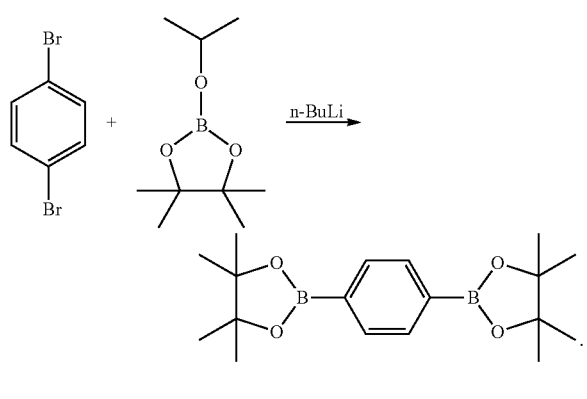

The oxygen-free environment is composed of nitrogen and inert gases.

In said preparing method of silafluorenyl metalloporphyrin-benzene organic semiconductor material, 2-bromo-9-substituted silafluorene is produced from 2-bromo silafluorene referring to the reference: Macromolecules 2002, 35, 3474; 2-formyl-9-substituted silafluorene is produced from 2-bromo-9-substituted silafluorene referring to the reference: Macromolecules 2006, 39, 456; the preparation of dipyrromethane, referring to the reference: Tetrahedron 1994, 39, 11427.

Further description of the present invention will be illustrated, which combined with embodiments and the drawings.

EXAMPLE 1

The present embodiment discloses a silafluorenyl metalloporphyrin-benzene organic semiconductor material having the following structure formula:

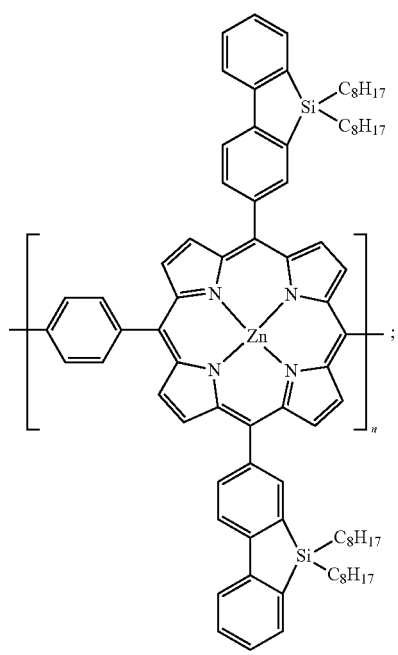

where n is 78;

the preparing method of said organic semiconductor material comprises:

firstly, synthesis of 1,4-p-bis(4,4,5,5-tetramethyl-1,3,2-dioxaborolan)benzene

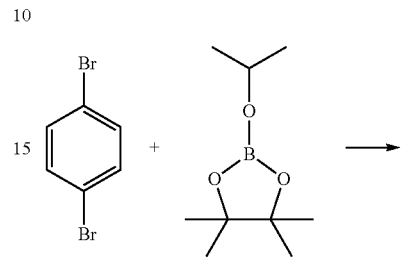

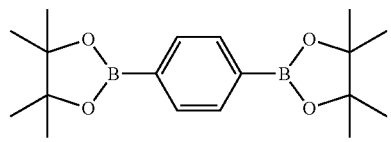

under the protection of nitrogen, adding p-dibromobenzene (4.8 g, 0.02 mol) into a three-necked flask, adding 100 mL of tetrahydrofuran (THF, similarly hereinafter) solvent, injecting n-butyl lithium (n-BuLi, 16.8 mL, 2.5M, 0.04 mol) at −78° C. with injector, continue to stir and react for 2 h, injecting 2-isopropoxy-4,4,5,5-tetramethyl-1,3,2-dioxaborolane (8.7 mL, 0.04 mol) at −78° C. with injector, stirring overnight at room temperature, adding saturated sodium chloride solution (30 ml) to terminate the reaction, extracting using chloroform, drying with anhydrous sodium sulfate, filtering, after that, collecting the filtrate liquid and rotary-evaporating solvent, in the end, raw product is purified by column chromatography on silica gel using a eluent of petroleum ether/acetone (15/1) to obtain product, the yield is 94.6%.

GC-MS (EI-m/z): 332(M$^+$)

secondly, synthesis of 5,15-bis(9',9'-dioctyl)silafluorenyl porphyrin

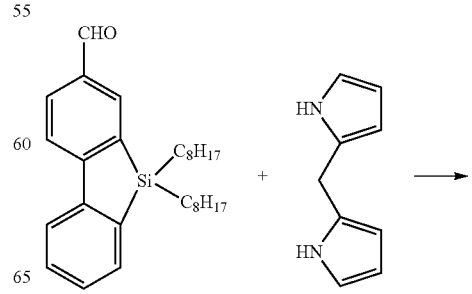

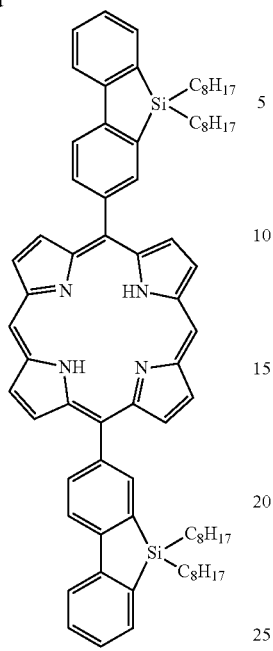

setting up the anhydrous and oxygen-free reactor, weighing the intermediate 2-formyl-9,9-dioctyl silafluorene (0.44 g, 1 mmol) and dipyrromethane (0.15 g, 1 mmol), dissolving in 250 mL of dichloromethane, supplying nitrogen for 30 min, adding 1 mL of propionic acid with injector, stirring at 20° C. for 24 h, then adding 2,3-dichloro-5,6-dicyano-1,4-benzoquinone (DDQ) (0.91 g, 4 mmol), continue to stir at room temperature for 30 min, then adding 1 mL of triethylamine to quench the reaction, concentrating solvent, filtering, collecting filtrate liquid and rotary-evaporating solvent, eluting rapidly on silica gel with dichloromethane, rotary-evaporating solvent, recrystallizing with diethyl ether/methanol to obtain product, the yield is about 85%.

GC-MS (EI-m/z): 1120(M⁺)

thirdly, synthesis of 5,15-dibromo-10,20-bis(9',9'-dioctyl) silafluorenyl porphyrin

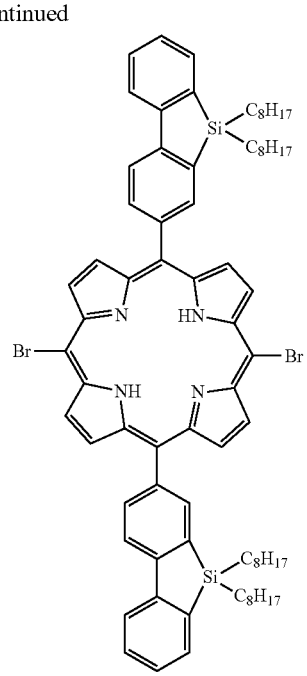

setting up the anhydrous and oxygen-free reactor, weighing 10,20-bis(9',9'-dioctyl)silafluorenyl porphyrin (0.23 g, 0.2 mmol) and dissolving in 80 mL of chloroform, adding 1 mL of pyridine, cooling the reactants to 0° C., adding N-bromobutanimide (0.07 g, 0 4 mmol), stirring for 72 h, after that, the mixture is allowed to reach room temperature, then continue to stir for 4 h, adding 5 mL of acetone to terminate the reaction, removing solvent, recrystallizing with diethyl ether/methanol to obtain product, the yield is 81%.

GC-MS (EI-m/z): 1278(M⁺)

fourthly, synthesis of 5,15-dibromo-10,20-bis(9',9'-dioctyl)silafluorenyl zincporphyrin

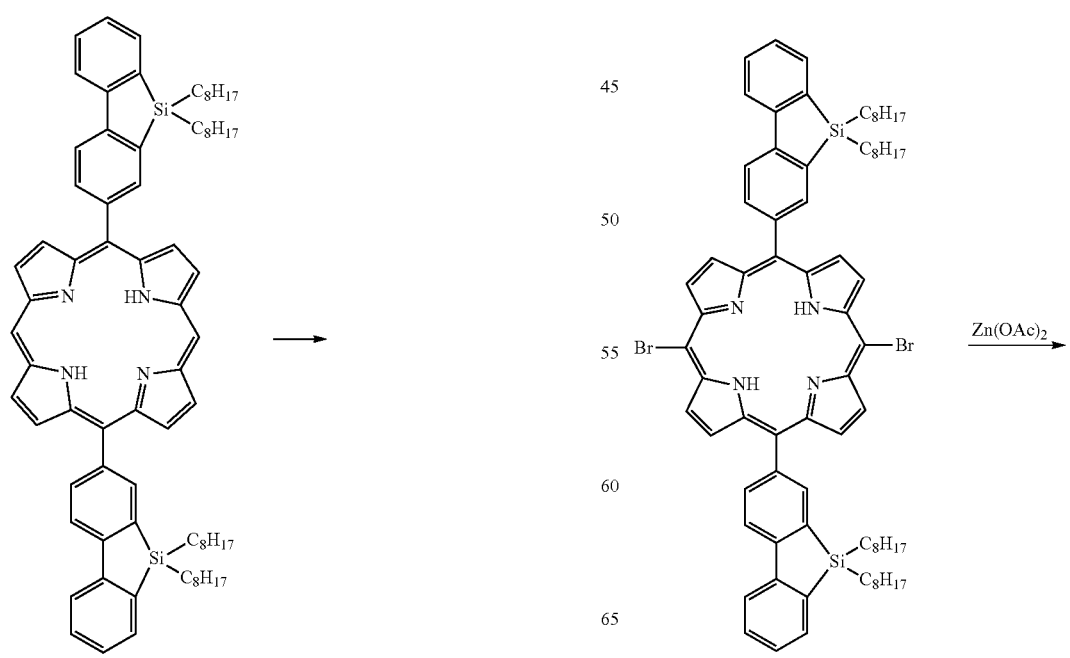

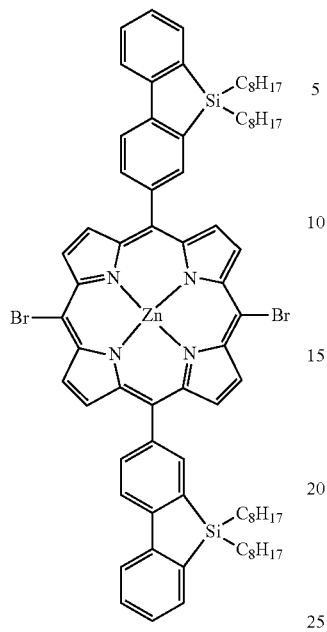

weighing the intermediate 5,15-dibromo-10,20-bis(9,9-dioctylfluorene)porphyrin (0.25 g, 0.2 mmol) and dissolving in 50 mL of dichloromethane, adding methanol solution (5 mL) containing zinc acetate (Zn(OAc)$_2$, 0.11 g, 0 5 mmol), stirring at room temperature for 5 h, rotary-evaporating solvent, then eluting on silica gel with dichloromethane/petroleum ether (1/1), collecting and rotary-evaporating solvent to obtain product, the yield is 94%.

GC-MS (EI-m/z): 1340(M$^+$)

fifthly, synthesis of silafluorenyl zincporphyrin-benzene organic semiconductor material

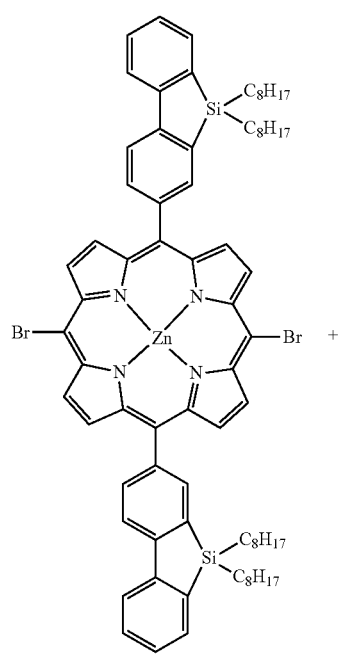 +

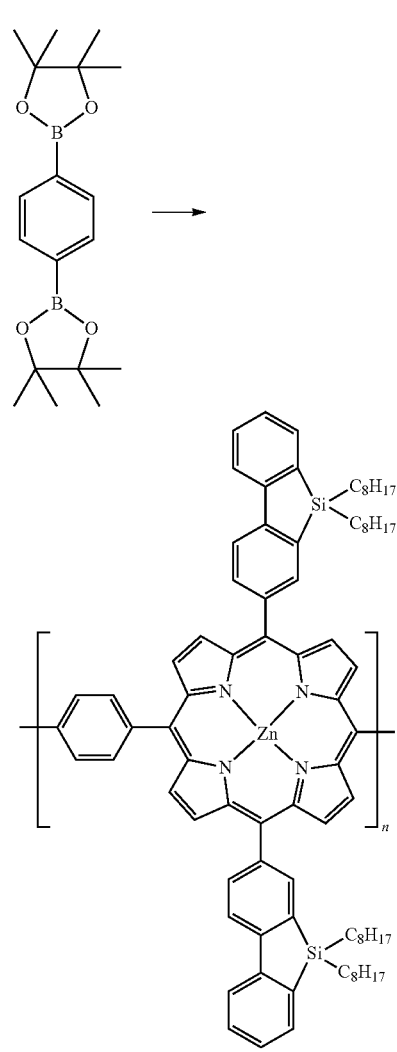

under the protection of nitrogen, adding 1,4-bis(4,4,5,5-tetramethyl-1,3,2-dioxaborolan)benzene (66 mg, 0 2 mmol), 5,15-dibromo-10,20-bis(9',9'-dioctyl)silafluorenyl zincporphyrin (268 mg, 0.2 mmol) and 50 mL of methylbenzene solvent, vacuumizing to remove oxygen and supplying nitrogen, then adding 5 mg of Pd(PPh$_3$)$_2$Cl$_2$ and 2 mL of NaHCO$_3$ (50%) solution, heating to 100° C. and reacting for 56 h to obtain mixed solution of reactants of silafluorenyl zincporphyrin-benzene organic semiconductor material.

cooling to room temperature, then dripping the mixed solution into 300 mL of methanol to settle, filtering, washing with methanol, drying; then dissolving with methylbenzene, adding into aqueous solution of sodium diethyldithiocarbamate, then heating the mixed solution to 80° C. and stirring overnight, organic phase is subjected to column chromatography on alumina eluting with chlorobenzene; removing the organic solvent under reduced pressure, settling with methanol, filtering, extracting the obtained solid with acetone in Soxhlet extractor for three days; settling with methanol, filtering, pumping overnight with vacuum pump to obtain silafluorenyl zincporphyrin-benzene organic semiconductor material as a solid product, the yield is 72%. Molecular weight (GPC, THF, R. I): Mn is 98000, Mw/Mn is 3.24;)

EXAMPLE 2

The present embodiment discloses a silafluorenyl ironporphyrin-benzene organic semiconductor material having the following structure formula:

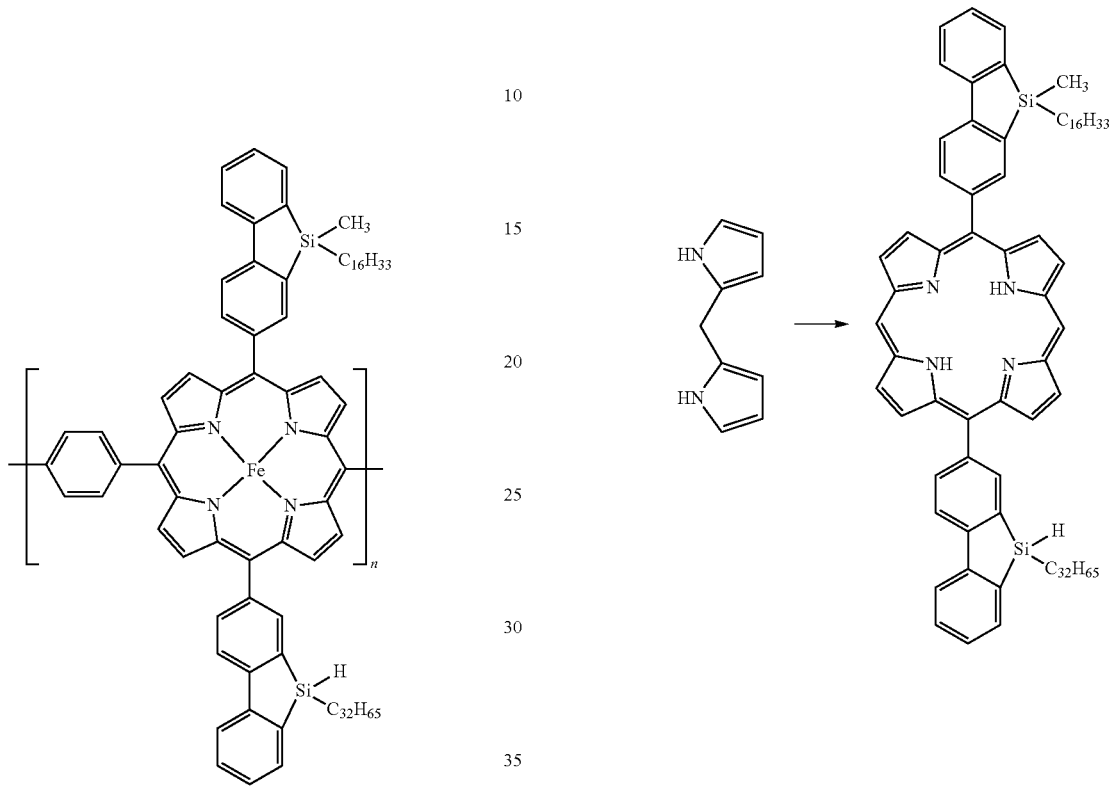

where n is 56;

the preparing method of said organic semiconductor material comprises:

firstly, synthesis of 1,4-bis(4,4,5,5-tetramethyl-1,3,2-dioxaborolan)benzene

For details about its preparation, see Example 1, but argon is employed as protection gas of oxygen-free environment.

secondly, synthesis of 5-(9'-methyl-9'-cetyl)silafluorenyl-15-(9'-dotriacontyl)silafluorenyl porphyrin

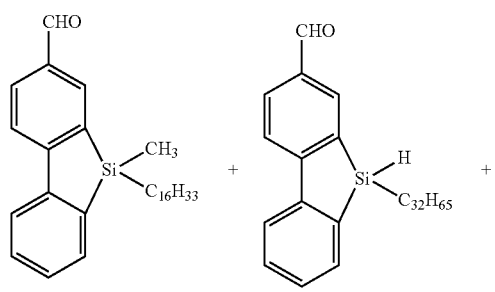

setting up the anhydrous and oxygen-free reactor, weighing the intermediate 2-formyl-9-methyl-9-cetyl silafluorene (0.45 g, 1 mmol), 2-formyl-9-dotriacontyl silafluorene (0.66 g, 1 mmol) and dipyrromethane (0.30 g, 2 mmol), dissolving in 250 mL of dichloromethane, supplying argon for 30 min, adding 2 mL of trifluoroacetic acid with injector, stirring at 100° C. for 1 h, then adding 2,3-dichloro-5,6-dicyano-1,4-benzoquinone (DDQ) (1.82 g, 8 mmol), continue to stir at room temperature for 30 min, then adding 2 mL of pyridine to quench the reaction, concentrating solvent, filtering, collecting filtrate liquid and rotary-evaporating solvent, eluting rapidly on silica gel with dichloromethane, rotary-evaporating solvent, recrystallizing with diethyl ether/methanol to obtain product, the yield is about 78%.

GC-MS (EI-m/z): 1359(M$^+$)

thirdly, synthesis of 5,15-dibromo-10-(9'-methyl-9'-cetyl)silafluorenyl-20-(9'-dotriacontyl)silafluorenyl porphyrin

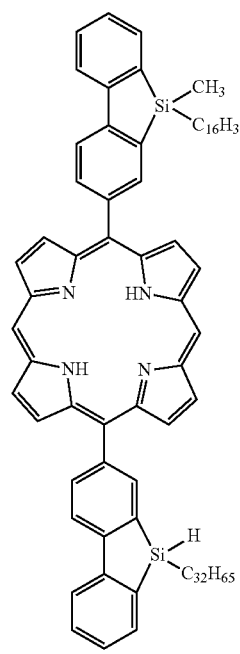

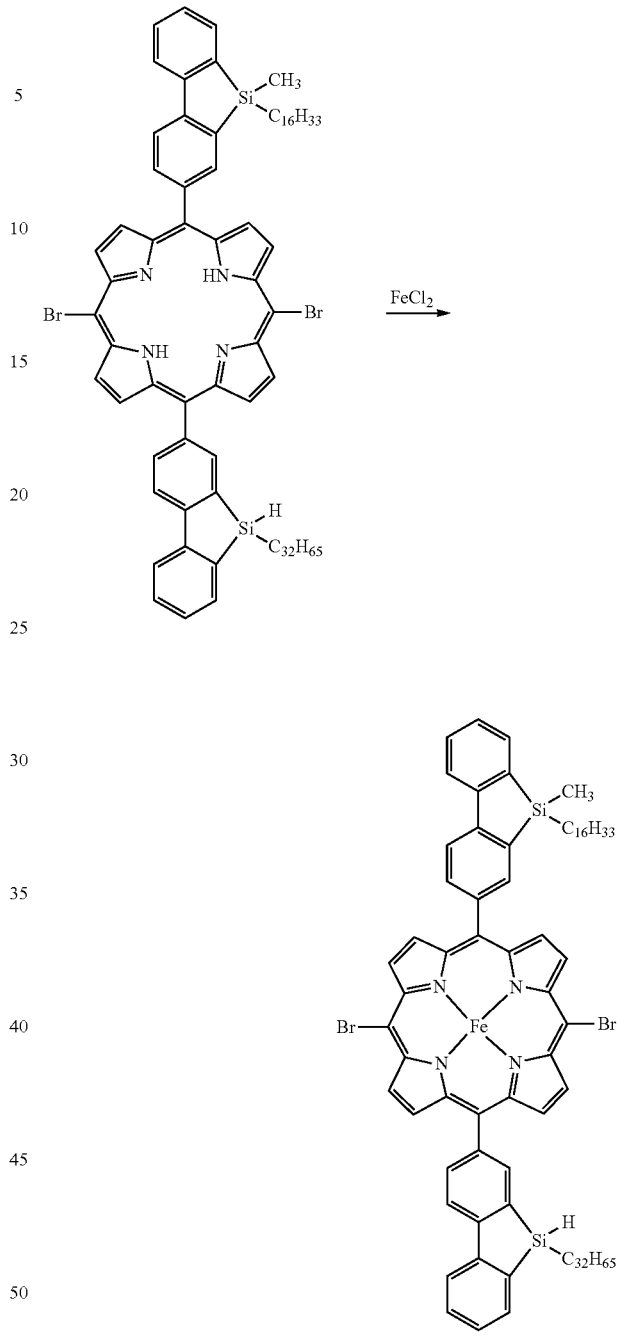

setting up the anhydrous and oxygen-free reactor, weighing 5-(9'-methyl-9'-cetyl)silafluorenyl-15-(9'-dotriacontyl)silafluorenyl porphyrin (0.27 g, 0 2 mmol) and dissolving in 80 mL of chloroform, adding 1 mL of pyridine, cooling the reactants to 0° C., adding N-bromobutanimide (0.07 g, 0.4 mmol), stirring for 0.5 h, after that, the mixture is warmed up to 120° C., then continue to stir for 1 h, adding 5 mL of acetone to terminate the reaction, removing solvent, recrystallizing with diethyl ether/methanol to obtain product, the yield is 79%.

GC-MS (EI-m/z): 1516(M$^+$)

fourthly, synthesis of 5,15-dibromo-10-(9'-methyl-9'-cetyl)silafluorenyl-20-(9'-dotriacontyl)silafluorenyl ironporphyrin in the presence of argon, weighing the intermediate 5,15-dibromo-10-(9'-methyl-9'-cetyl)silafluorenyl-20-(9'-dotriacontyl)silafluorenyl porphyrin (0.31 g, 0.2 mmol) and dissolving in 50 mL of dichloromethane, adding methanol solution (5 mL) containing ferrous chloride (0.12 g, 1 mmol), stirring at room temperature for 8 h, rotary-evaporating solvent, then eluting on silica gel with dichloromethane/petroleum ether (1/1), collecting and rotary-evaporating solvent to obtain product, the yield is 95%.

GC-MS (EI-m/z): 1569(M$^+$)

fifthly, synthesis of silafluorenyl ironporphyrin-benzene organic semiconductor material

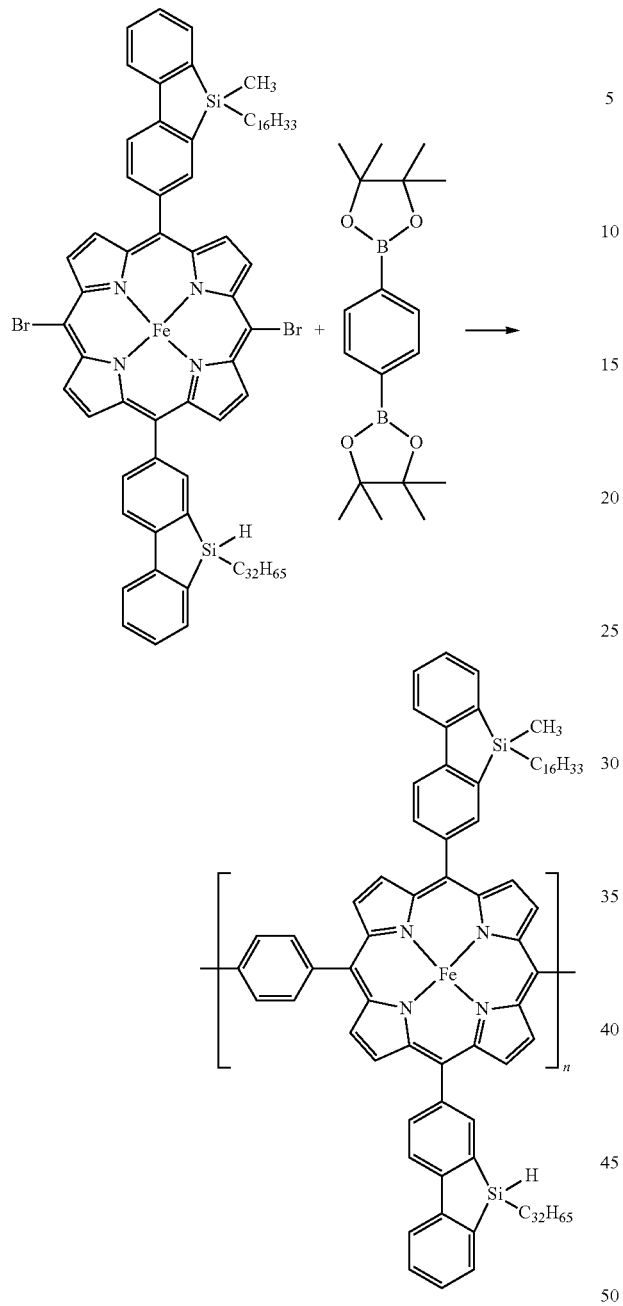

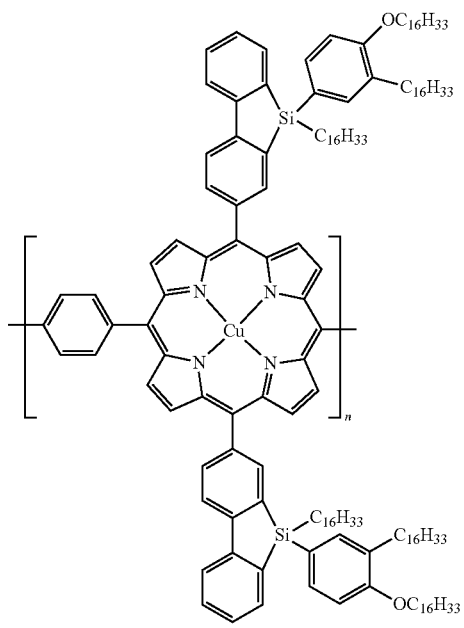

night, organic phase is subjected to column chromatography on alumina eluting with chlorobenzene; removing the organic solvent under reduced pressure, settling with methanol, filtering, extracting the obtained solid with acetone in Soxhlet extractor for three days; settling with methanol, filtering, pumping overnight with vacuum pump to obtain silafluorenyl ironporphyrin-benzene organic semiconductor material as a solid product, the yield is 74%. Molecular weight (GPC, THF, R. I): Mn is 87000, Mw/Mn is 3.63;)

EXAMPLE 3

The present embodiment discloses a silafluorenyl copperporphyrin-benzene organic semiconductor material having the following structure formula:

where n is 28;

the preparing method of said organic semiconductor material comprises:

firstly, synthesis of 1,4-bis(4,4,5,5-tetramethyl-1,3,2-dioxaborolan)benzene

For details about its preparation, see Example 1.

secondly, synthesis of 10,20-bis(9'-cetyl-9'-(3"-cetyl-4"-cetyloxy)phenyl)silafluorenyl porphyrin under the protection of nitrogen, adding 1,4-bis(4,4,5,5-tetramethyl-1,3,2-dioxaborolan)benzene (66 mg, 0.2 mmol), 5,15-dibromo-10-(9'-methyl-9'-cetyl)silafluorenyl-20-(9'-dotriacontyl)silafluorenyl ironporphyrin (314 mg, 0.2 mmol) and 120 mL of methylbenzene solvent, vacuumizing to remove oxygen and supplying argon, then adding Pd(OAc)$_2$ (2.5 mg)/tricyclohexyl phosphine (6.5 mg) and 2 mL of 20% (wt) tetraethyl ammonium hydroxide (Et$_4$NOH, similarly hereinafter) solution, heating to 120° C. and reacting for 24 h to obtain mixed solution of reactants of silafluorenyl ironporphyrin-benzene organic semiconductor material.

cooling to room temperature, then dripping the mixed solution into 200 mL of methanol to settle, filtering, washing with methanol, drying; then dissolving with methylbenzene, adding into aqueous solution of sodium diethyldithiocarbamate, then heating the mixed solution to 80° C. and stirring over-

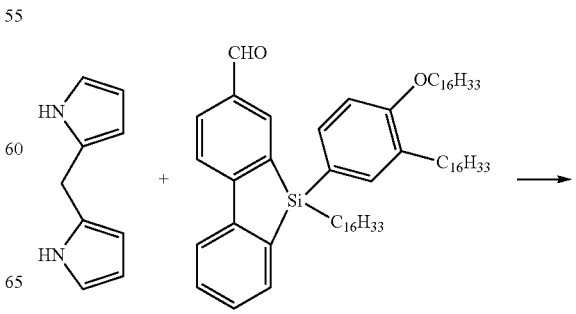

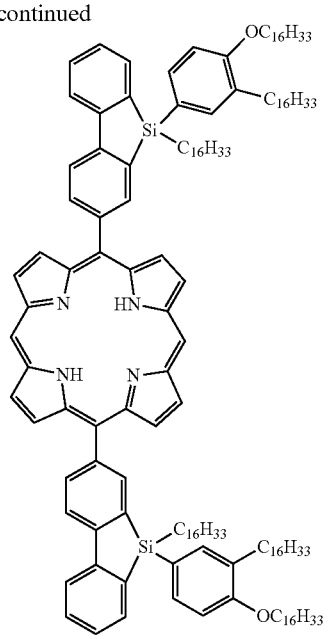

setting up the anhydrous and oxygen-free reactor, weighing the intermediate 2-formyl-9-cetyl-9-(3'-cetyl-4'-cetyloxy)phenyl)silafluorene (1.95 g, 2 mmol) and dipyrromethane (0.30 g, 2 mmol), dissolving in 300 mL of dichloromethane, supplying nitrogen for 30 min, adding 2 mL of trifluoroacetic acid with injector, stirring at room temperature for 3 h, then adding 2,3-dichloro-5,6-dicyano-1,4-benzoquinone (DDQ) (1.82 g, 8 mmol), continue to stir at room temperature for 30 min, then adding 2 mL of triethylamine to quench the reaction, concentrating solvent, filtering, collecting filtrate liquid and rotary-evaporating solvent, eluting rapidly on silica gel with dichloromethane, rotary-evaporating solvent, recrystallizing with diethyl ether/methanol to obtain product, the yield is about 85%.

GC-MS (EI-m/z): 2201(M$^+$)

thirdly, synthesis of 5,15-dibromo-10,20-bis(9'-cetyl-9'-(3"-cetyl-4"-cetyloxy)phenyl)silafluorenyl porphyrin

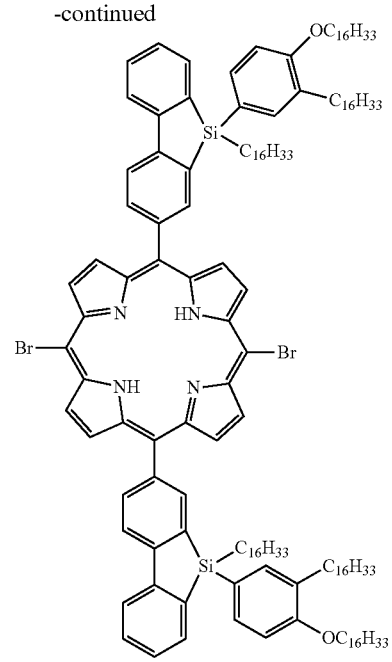

setting up the anhydrous and oxygen-free reactor, weighing 10,20-bis(9'-cetyl-9'-(3"-cetyl-4"-cetyloxy)phenyl)silafluorenyl porphyrin (0.44 g, 0.2 mmol) and dissolving in 80 mL of chloroform, adding 1 mL of pyridine, cooling the reactants to 0° C., adding N-bromobutanimide (0.07 g, 0.4 mmol), stirring for 0.5 h, after that, the mixture is allowed to reach 30° C., then continue to stir for 48 h, adding 5 mL of acetone to terminate the reaction, removing solvent, recrystallizing with diethyl ether/methanol to obtain product, the yield is 76%.

GC-MS (EI-m/z): 2360(M$^+$)

fourthly, synthesis of 5,15-dibromo-10,20-bis(9'-cetyl-9'-(3"-cetyl-4"-cetyloxy)phenyl)silafluorenyl copperporphyrin

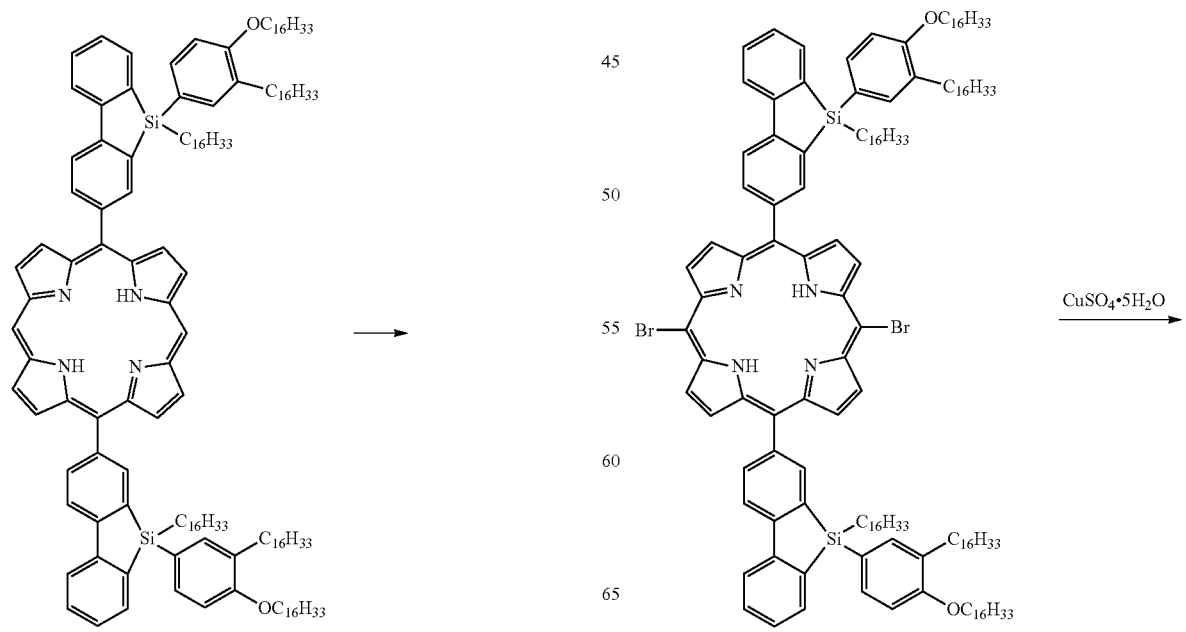

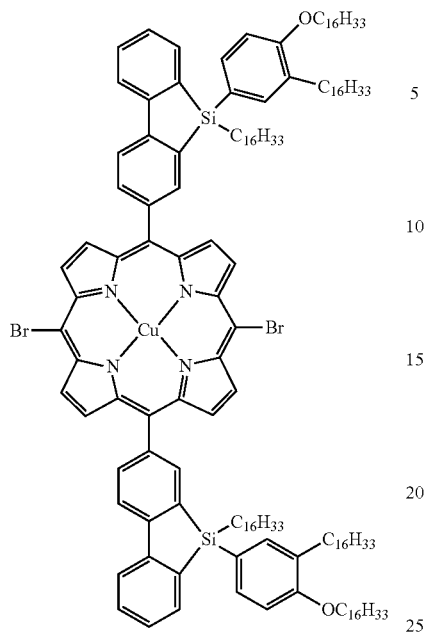

weighing the intermediate 5,15-dibromo-10,20-bis(9'-cetyl-9'-(3"-cetyl-4"-cetyloxy)phenyl)silafluorenyl porphyrin (0.47 g, 0.2 mmol) and dissolving in 50 mL of dichloromethane, adding CuSO$_4$·5H$_2$O (0.05 g, 0.2 mmol) solution (5 ml), stirring at room temperature for 5 h, rotary-evaporating solvent, then eluting on silica gel with dichloromethane/petroleum ether (1/1), collecting and rotary-evaporating solvent to obtain product, the yield is 93%.

GC-MS (EI-m/z): 2416(M$^+$)

fifthly, synthesis of silafluorenyl copperporphyrin-benzene organic semiconductor material

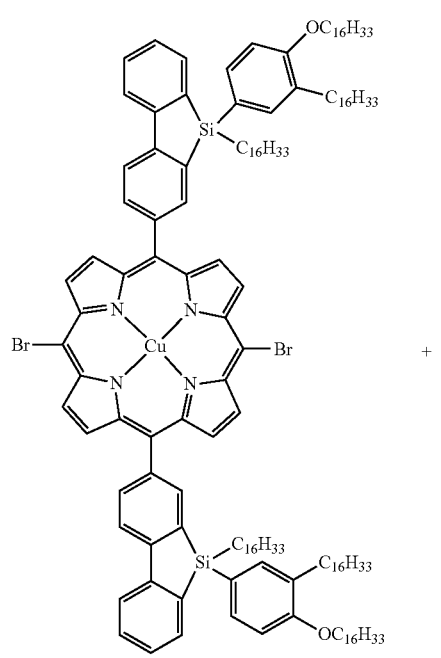

+

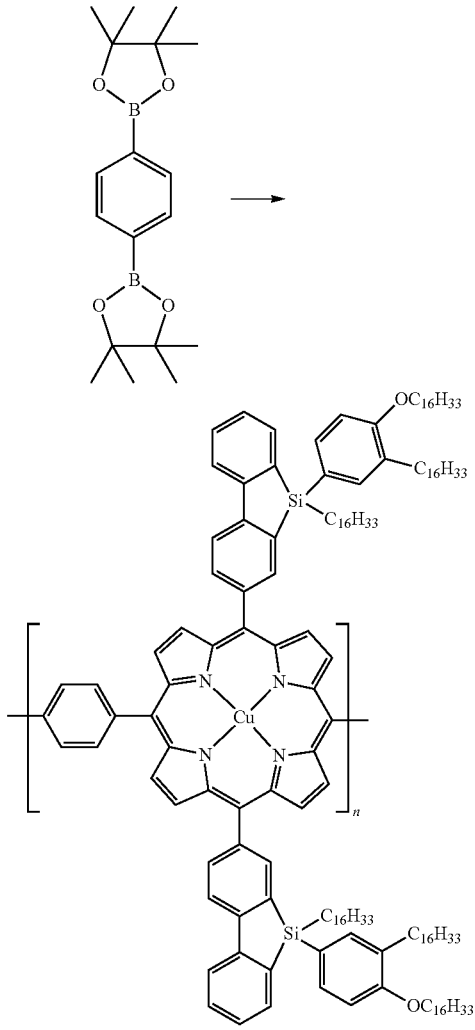

under the protection of nitrogen, adding 1,4-bis(4,4,5,5-tetramethyl-1,3,2-dioxaborolan)benzene (66 mg, 0.2 mmol), 5,15-dibromo-10,20-bis(9'-cetyl-9'-(3"-cetyl-4"-cetyloxy)phenyl)silafluorenyl copperporphyrin (483 mg, 0.2 mmol) and 100 mL of methylbenzene solvent, vacuumizing to remove oxygen and supplying nitrogen, then adding 10 mg of Pd(PPh$_3$)$_2$Cl$_2$ and 2 ml of KHCO$_3$(30%) solution, heating to 50° C. and reacting for 72 h to obtain mixed solution of reactants of silafluorenyl copperporphyrin-benzene organic semiconductor material.

cooling to room temperature, then dripping the mixed solution into 300 mL of methanol to settle, filtering, washing with methanol, drying; then dissolving with methylbenzene, adding into aqueous solution of sodium diethyldithiocarbamate, then heating the mixed solution to 80° C. and stirring overnight, organic phase is subjected to column chromatography on alumina eluting with chlorobenzene; removing the organic solvent under reduced pressure, settling with methanol, filtering, extracting the obtained solid with acetone in Soxhlet extractor for three days; settling with methanol, filtering, pumping overnight with vacuum pump to obtain silafluorenyl copperporphyrin-benzene organic semiconductor material as a solid product, the yield is 82%. Molecular weight (GPC, THF, R. I): Mn is 65400, Mw/Mn is 3.18;)

EXAMPLE 4

The present embodiment discloses a silafluorenyl cadmiumporphyrin-benzene organic semiconductor material having the following structure formula:

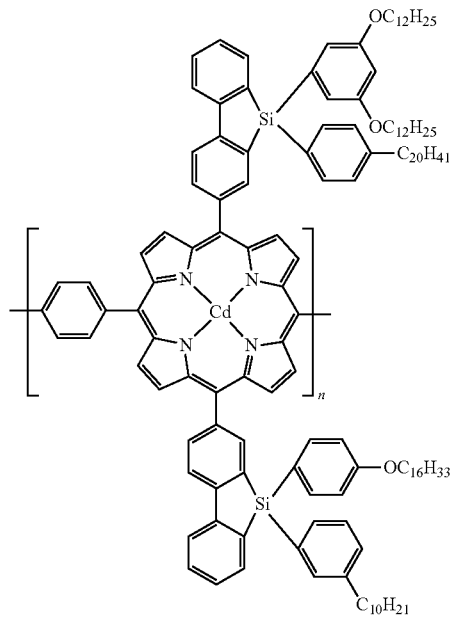

where n is 100;

the preparing method of said organic semiconductor material comprises:

firstly, synthesis of 1,4-bis(4,4,5,5-tetramethyl-1,3,2-dioxaborolan)benzene

For details about its preparation, see Example 1.

secondly, synthesis of 5-(9'-p-eicosyl-9'-(3",5"-didodecyloxy phenyl))silafluorenyl-15-(9'-p-cetyloxy phenyl-9'-m-decyl phenyl)silafluorenyl porphyrin

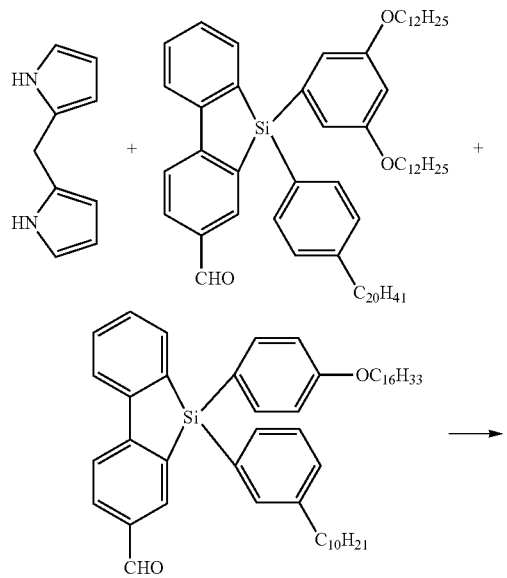

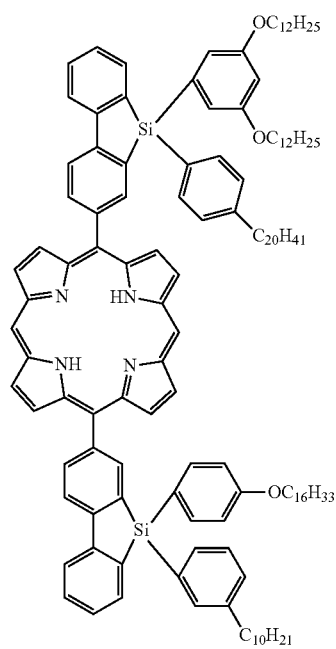

setting up the anhydrous and oxygen-free reactor, weighing the intermediate 2-formyl-9-p-eicosyl phenyl-9-(3',5'-didodecyloxy phenyl)silafluorenyl (1.02 g, 1 mmol), 2-formyl-9-p-cetyloxy phenyl-9-m-decyl phenyl silafluorenyl (0.74 g, 1 mmol) and dipyrromethane (0.30 g, 2 mmol), dissolving in 250 mL of dichloromethane, supplying nitrogen for 30 min, adding 1 mL of acetic acid with injector, stirring at 20° C. for 24 h, then adding 2,3-dichloro-5,6-dicyano-1,4-benzoquinone (DDQ) (0.91 g, 4 mmol), continue to stir at room temperature for 30 min, then adding 1 mL of triethylamine to quench the reaction, concentrating solvent, filtering, collecting filtrate liquid and rotary-evaporating solvent, eluting rapidly on silica gel with dichloromethane, rotary-evaporating solvent, recrystallizing with diethyl ether/methanol to obtain product, the yield is about 83%.

GC-MS (EI-m/z): 2205(M$^+$)

thirdly, synthesis of 5,15-dibromo-10-(9'-p-eicosyl phenyl-9'-(3",5"-didodecyloxy phenyl))silafluorenyl-20-(9'-p-cetyloxy phenyl-9'-m-decyl phenyl)silafluorenyl porphyrin

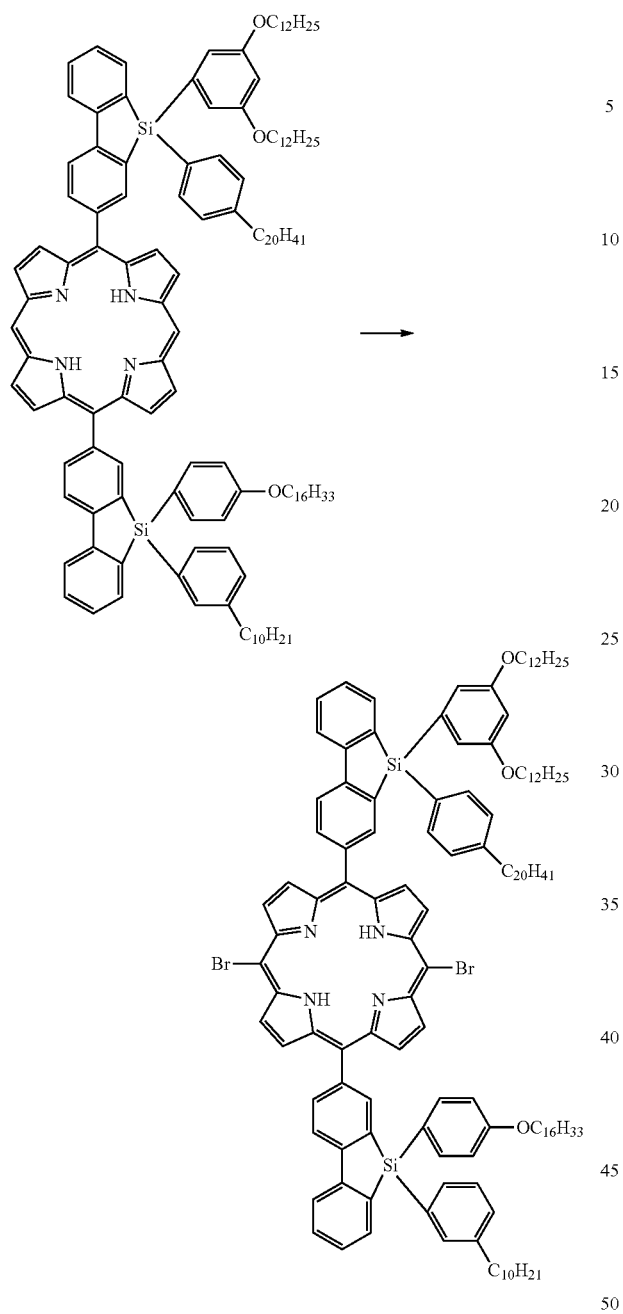

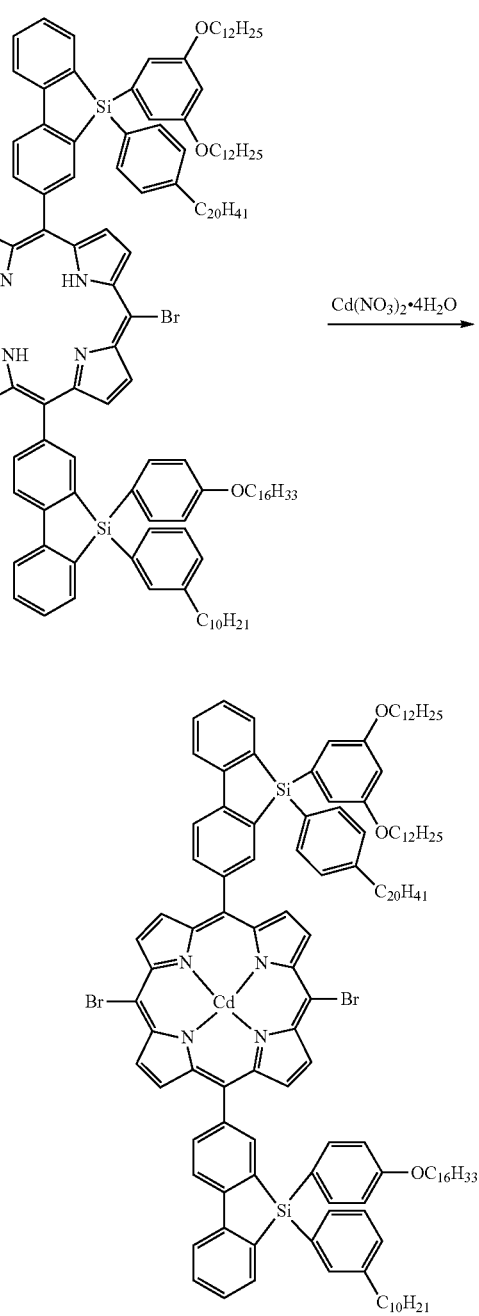

setting up the anhydrous and oxygen-free reactor, weighing 5,15-dibromo-10-(9'-p-eicosyl phenyl-9'-(3",5"-didodecyloxy phenyl))silafluorenyl-20-(9'-p-cetyloxy phenyl-9'-m-decyl phenyl)silafluorenyl porphyrin (0.44 g, 0.2 mmol) and dissolving in 80 mL of dimethylformamide(DMF), cooling the reactants to 0° C., adding N-bromobutanimide (0.07 g, 0.4 mmol), stirring for 72 h, after that, the mixture is warmed up to room temperature, then continue to stir for 4 h, adding 5 mL of acetone to terminate the reaction, removing solvent, recrystallizing with diethyl ether/methanol to obtain product, the yield is 83%.

GC-MS (EI-m/z): 2162(M+)

fourthly, synthesis of 5,15-dibromo-10-(9'-p-eicosyl phenyl-9'-(3",5"-didodecyloxy phenyl)silafluorenyl-20-(9'-p-cetyloxy phenyl-9'-m-decyl phenyl)silafluorenyl cadmiumporphyrin weighing the intermediate 5,15-dibromo-10-(9'-p-eicosyl phenyl-9'-(3",5"-didodecyloxy phenyl))silafluorenyl-20-(9'-p-cetyloxy phenyl-9'-m-decyl phenyl)silafluorenyl porphyrin (0.43 g, 0.2 mmol) and dissolving in 50 mL of dichloromethane, adding methanol solution (5 ml) of Cd(NO₃)₂·4H₂O (0.31 g, 1 mmol), stirring at room temperature for 5 h, rotary-evaporating solvent, then eluting on silica gel with dichloromethane/petroleum ether (1/1), collecting and rotary-evaporating solvent to obtain product, the yield is 94%.

GC-MS (EI-m/z): 2271(M+)

fifthly, synthesis of silafluorenyl cadmiumporphyrin-benzene organic semiconductor material

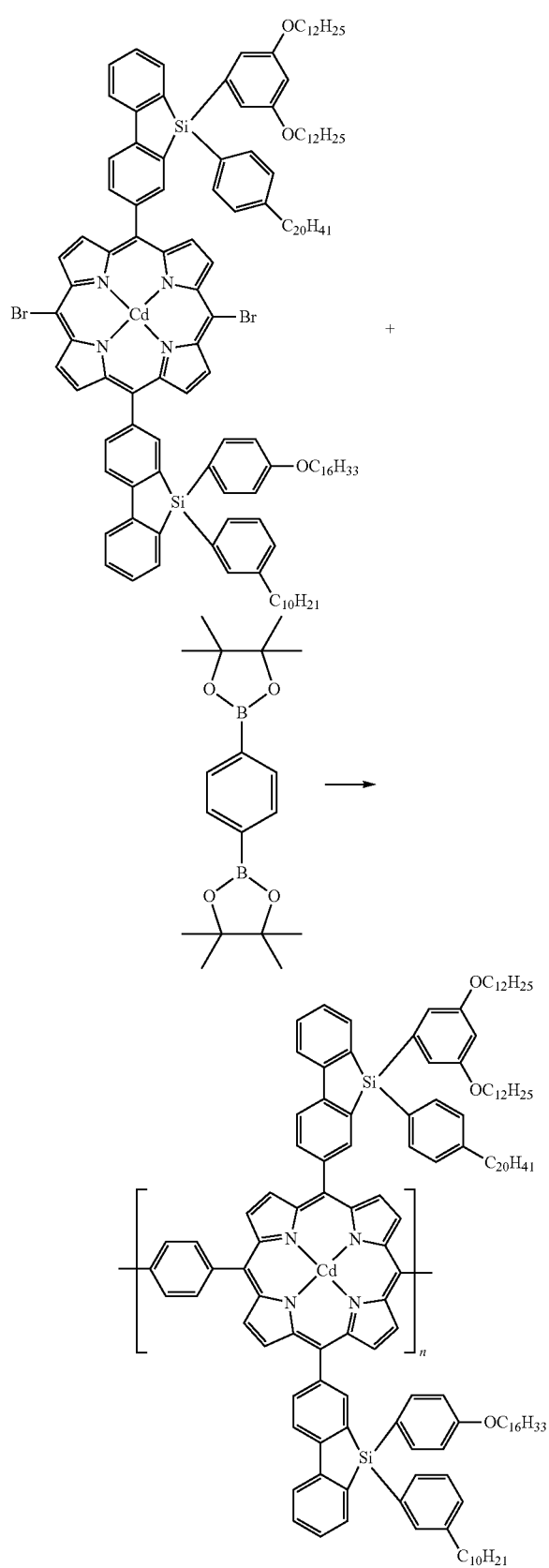

under the protection of nitrogen, adding 1,4-bis(4,4,5,5-tetramethyl-1,3,2-dioxaborolan)benzene (66 mg, 0.2 mmol), 5,15-dibromo-10-(9'-p-eicosyl phenyl-9'-(3",5"-didodecyloxy phenyl))silafluorenyl-20-(9'-p-cetyloxy phenyl-9'-m-decyl phenyl)silafluorenyl porphyrin (454 mg, 0.2 mmol) and 60 mL of dioxane solvent, vacuumizing to remove oxygen and supplying nitrogen, then adding $Pd_2(dba)_3$ (5 mg)/P(o-Tol)$_3$ (8 mg) and 15% $Na_2CO_3$(3 ml) solution, heating to 80° C. and reacting for 36 h to obtain mixed solution of reactants of silafluorenyl cadmiumporphyrin-benzene organic semiconductor material.

cooling to room temperature, then dripping the mixed solution into 250 mL of methanol to settle, filtering, washing with methanol, drying; then dissolving with methylbenzene, adding into aqueous solution of sodium diethyldithiocarbamate, then heating the mixed solution to 80° C. and stirring overnight, organic phase is subjected to column chromatography on alumina eluting with chlorobenzene; removing the organic solvent under reduced pressure, settling with methanol, filtering, extracting the obtained solid with acetone in Soxhlet extractor for three days; settling with methanol, filtering, pumping overnight with vacuum pump to obtain silafluorenyl cadmiumporphyrin-benzene organic semiconductor material as a solid product, the yield is 75%. Molecular weight (GPC, THF, R. I): Mn is 219000, Mw/Mn is 4.36;

EXAMPLE 5

The present embodiment discloses a silafluorenyl cobalt-porphyrin-benzene organic semiconductor material having the following structure formula:

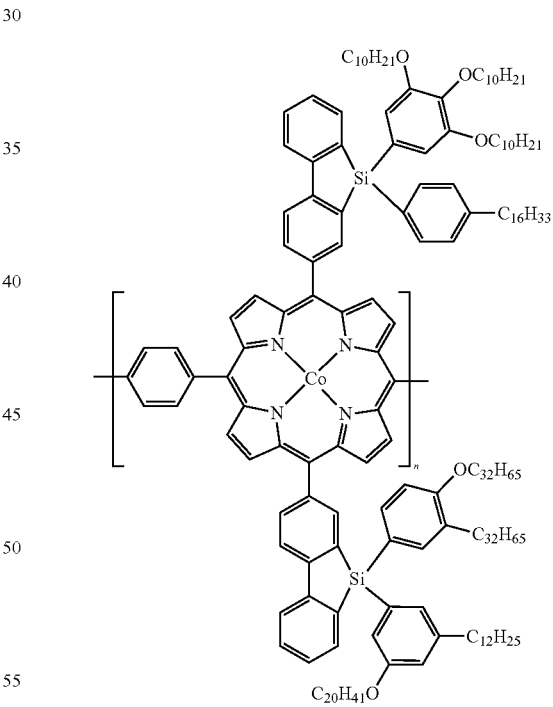

where n is 40;

the preparing method of said organic semiconductor material comprises:

firstly, synthesis of 1,4-bis(4,4,5,5-tetramethyl-1,3,2-dioxaborolan)benzene

For details about its preparation, see Example 1.

secondly, synthesis of 5-(9'-(3",4",5"-tridecyloxy)phenyl-9'-p-cetyl phenyl)silafluorenyl-15-(9'-(3"-dodecyl-5"-eicosyloxy)phenyl-9'-(3"-dotriacontyl-4"-dotriacontyloxy)phenyl)silafluorenyl porphyrin

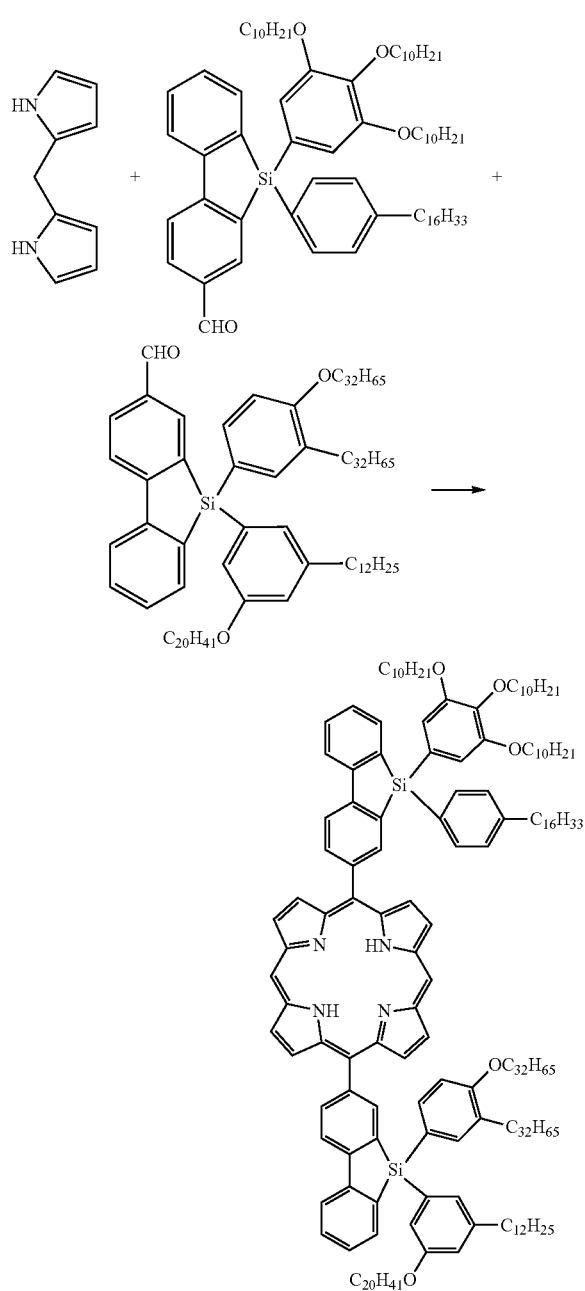

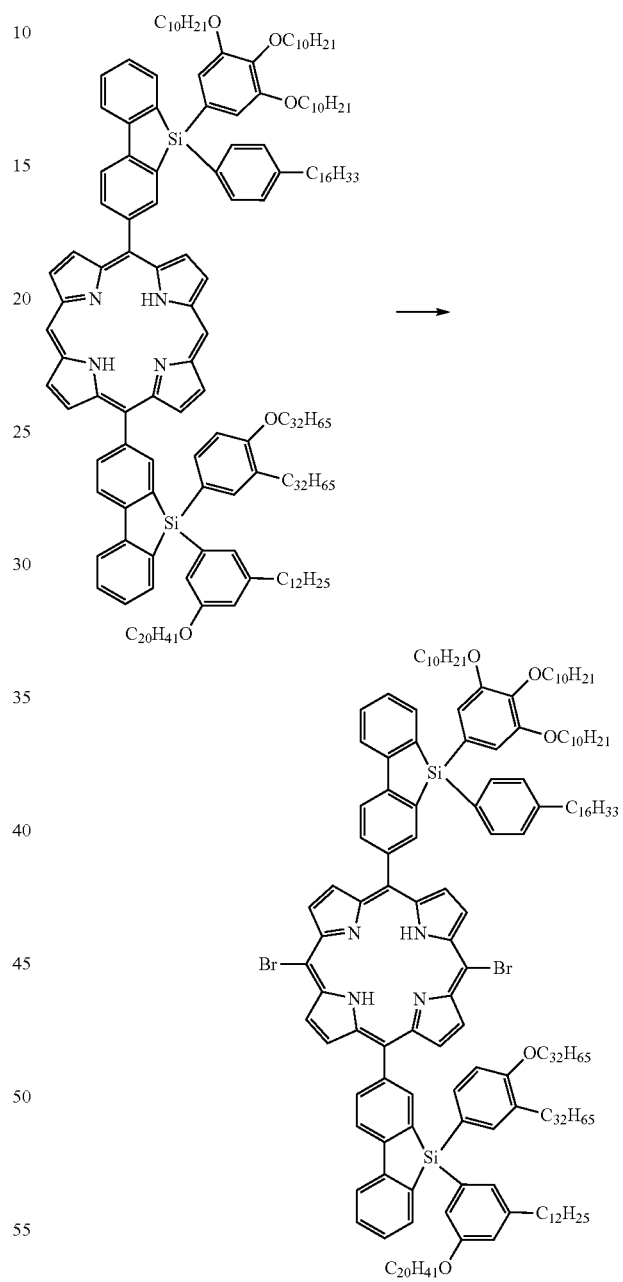

setting up the anhydrous and oxygen-free reactor, weighing the intermediate 2-formyl-9-(3',4',5'-tridecyloxy)beneze-9-p-cetyl phenyl silafluorenyl (1.06 g, 1 mmol), 2-formyl-9-(3'-dodecyl-5'-eicosyloxy)-9-(3'-dotriacontyl-4'-dotriacontyloxy)phenyl silafluorenyl porphyrin (1.74 g, 1 mmol) and dipyrromethane (0.30 g, 2 mmol), dissolving in 250 mL of dichloromethane, supplying nitrogen for 30 min, adding 2 mL of acetic acid with injector, stirring at 100° C. for 1 h, then adding 2,3-dichloro-5,6-dicyano-1,4-benzoquinone (DDQ) (1.82 g, 8 mmol), continue to stir at room temperature for 30 min, then adding 2 mL of pyridine to quench the reaction, concentrating solvent, filtering, collecting filtrate liquid and rotary-evaporating solvent, eluting rapidly on silica gel with dichloromethane, rotary-evaporating solvent, recrystallizing with diethyl ether/methanol to obtain product, the yield is about 74%.

GC-MS (EI-m/z): 3047(M⁺)

thirdly, synthesis of 5,15-dibromo-10-(9'-(3",4",5"-tridecyloxy)phenyl-9'-p-cetyl phenyl)silafluorenyl-20-(9'-(3"-dodecyl-5"-eicosyloxy)phenyl-9'-(3"-dotriacontyl-4"-dotriacontyloxy)phenyl)silafluorenyl porphyrin setting up the anhydrous and oxygen-free reactor, weighing 5-(9'-3",4",5"-tridecyloxy)phenyl-9'-p-cetyl phenyl)silafluorenyl-15-(9'-(3"-dodecyl-5"-eicosyloxy)phenyl-9'-(3"-dotriacontyl-4"-dotriacontyloxy)phenyl)silafluorenyl porphyrin (0.61 g, 0.2 mmol) and dissolving in 40 mL of tetrahydrofuran, adding 0.5 mL of triethylamine, cooling the reactants to 0° C., adding N-bromobutanimide (0.07 g, 0.4 mmol), stirring for 0.5 h, after that, the mixture is warmed up to reflux, then continue to stir for 1 h, adding 5 mL of acetone to terminate the reaction, removing solvent, recrystallizing with diethyl ether/methanol to obtain product, the yield is 82%.

GC-MS (EI-m/z): 3204(M+)

fourthly, synthesis of 5-(9'-(3",4",5"-tridecyloxy)phenyl-9'-p-cetyl phenyl)silafluorenyl-15-(9'-(3" dodecyl-5"-eicosyloxy)phenyl-9'-(3"-dotriacontyl-4"-dotriacontyloxy)phenyl) silafluorenyl cobaltporphyrin weighing the intermediate 5-(9'-(3",4",5"-tridecyloxy) phenyl-9'-p-cetyl phenyl)silafluorenyl-15-(9'-(3"-dodecyl-5"-eicosyloxy)phenyl-9'-(3"-dotriacontyl-4"-dotriacontyloxy)phenyl)silafluorenyl porphyrin (0.64 g, 0.2 mmol) and dissolving in 50 mL of dichloromethane, adding CoCl$_2$.6H$_2$O (0.12 g, 0.5 mmol) solution (5 ml), stirring at room temperature for 12 h, rotary-evaporating solvent, then eluting on silica gel with dichloromethane/petroleum ether (1/1), collecting and rotary-evaporating solvent to obtain product, the yield is 96%.

GC-MS (EI-m/z): 3257(M+)

fifthly, synthesis of silafluorenyl cobaltporphyrin-phenyl organic semiconductor material

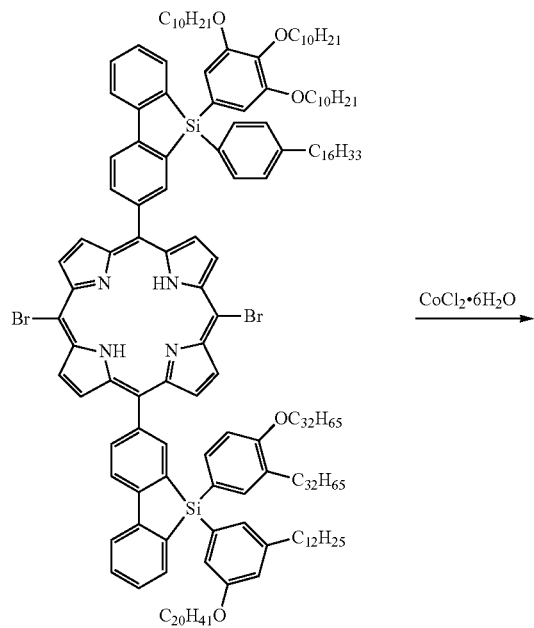

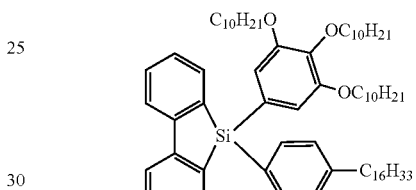

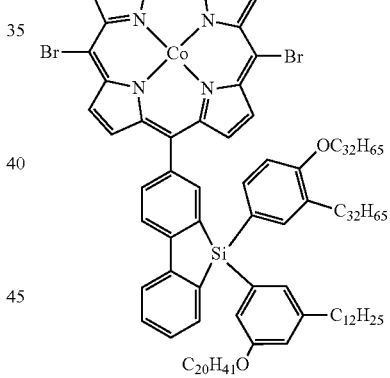

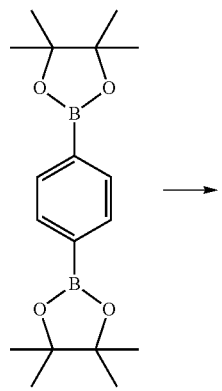

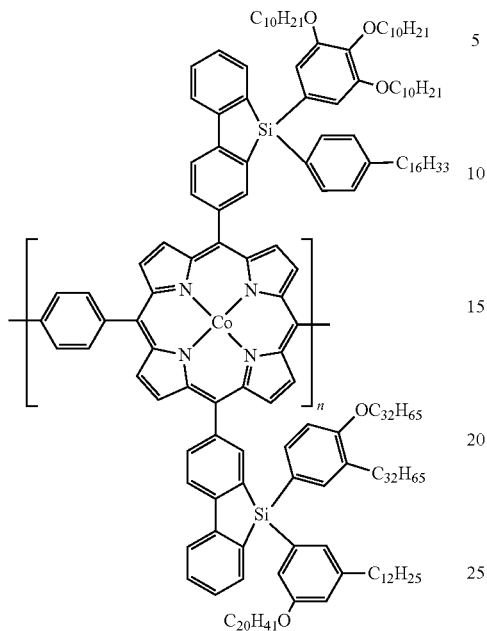

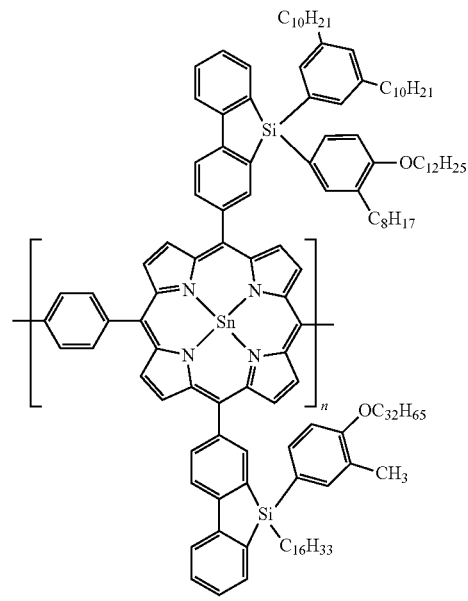

where n is 10;

the preparing method of said organic semiconductor material comprises:

firstly, synthesis of 1,4-bis(4,4,5,5-tetramethyl-1,3,2-dioxaborolan)benzene

For details about its preparation, see Example 1.

secondly, synthesis of 5-(9'-cetyl-9'-(3"-methyl-4"-dotriacontyloxy)phenyl)silafluorenyl-15-(9'-(3",5"-didecyl)phenyl-9'-(3"-octyl-4"-dodecyloxy)phenyl)silafluorenyl porphyrin

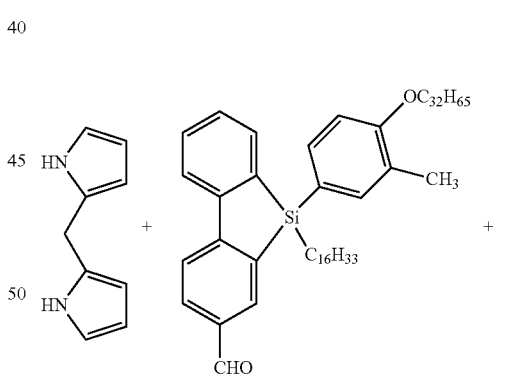

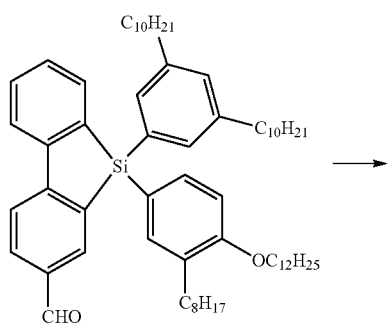

under the protection of nitrogen, adding 1,4-bis(4,4,5,5-tetramethyl-1,3,2-dioxaborolan)benzene (66 mg, 0.2 mmol), 5,15-dibromo-10-(9'-(3",4",5"-tridecyloxy)phenyl-9'-p-cetyl phenyl)silafluorenyl-20-(9'-(3"-dodecyl-5"-eicosyloxy)phenyl-9'-(3"-dotriacontyl-4"-dotriacontyloxy)phenyl) silafluorenyl cobaltporphyrin (650 mg, 0.2 mmol) and 80 mL of DMF solvent, vacuumizing to remove oxygen and supplying nitrogen, then adding Pd(OAc)$_2$ (2.5 mg)/tricyclohexyl phosphine (6.5 mg) and 2 mL of 20% (wt %) Et$_4$NOH solution, heating to 80° C. and reacting for 48 h to obtain mixed solution of reactants of silafluorenyl cobaltporphyrin-benzene organic semiconductor material.

cooling to room temperature, then dripping the mixed solution into 250 mL of methanol to settle, filtering, washing with methanol, drying; then dissolving with methylbenzene, adding into aqueous solution of sodium diethyldithiocarbamate, then heating the mixed solution to 80° C. and stirring overnight, organic phase is subjected to column chromatography on alumina eluting with chlorobenzene; removing the organic solvent under reduced pressure, settling with methanol, filtering, extracting the obtained solid with acetone in Soxhlet extractor for three days; settling with methanol, filtering, pumping overnight with vacuum pump to obtain silafluorenyl cobaltporphyrin-benzene organic semiconductor material as a solid product, the yield is 83%. Molecular weight (GPC, THF, R. I): Mn is 127100, Mw/Mn is 3.96.

EXAMPLE 6

The present embodiment discloses a silafluorenyl tinporphyrin-benzene organic semiconductor material having the following structure formula:

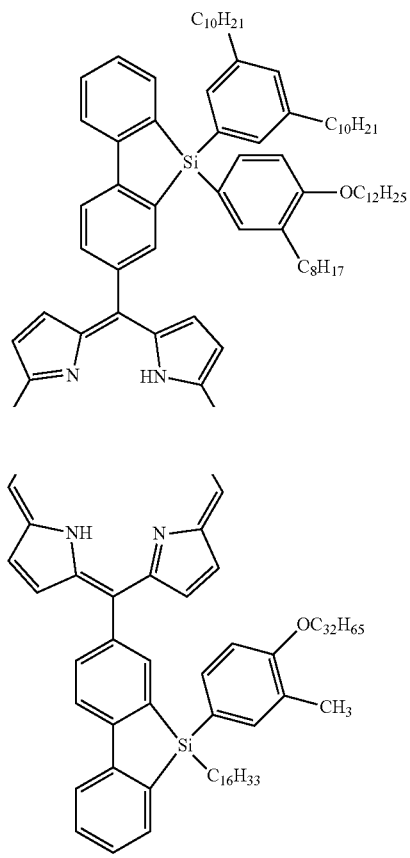

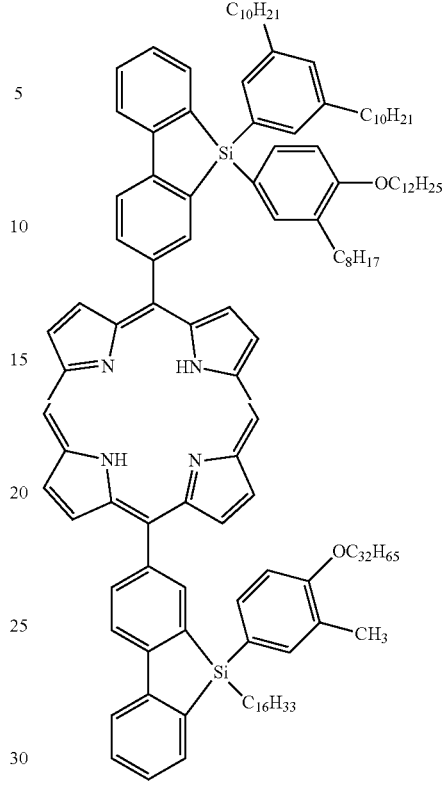

setting up the anhydrous and oxygen-free reactor, weighing the intermediate 2-formyl-9-cetyl-9-(3'-methyl-4'-dotriacontyl)phenyl silafluorenyl (0.99 g, 1 mmol), 2-formyl-9-(3', 5'-didecyl)phenyl-9-(3'-octyl-4'-dodecyloxy)phenyl silafluorene (0.94 g, 1 mmol) and dipyrromethane (0.30 g, 2 mmol), dissolving in 250 mL of dichloromethane, supplying nitrogen for 30 min, adding 2 mL of trifluoroacetic acid with injector, stirring at 100° C. for 1 h, then adding 2,3-dichloro-5,6-dicyano-1,4-benzoquinone (DDQ) (1.82 g, 8 mmol), continue to stir at room temperature for 30 min, then adding 2 mL of triethylamine to quench the reaction, concentrating solvent, filtering, collecting filtrate liquid and rotary-evaporating solvent, eluting rapidly on silica gel with dichloromethane, rotary-evaporating solvent, recrystallizing with diethyl ether/methanol to obtain product, the yield is about 74%.

GC-MS (EI-m/z): 2179(M+)

thirdly, synthesis of 5,15-dibromo-10-(9'-cetyl-9'-(3"-methyl-4"-dotriacontyloxy)phenyl)silafluorenyl-20-(9'-(3",5"-didecyl)phenyl-9'-(3"-octyl-4"-dodecyloxy)phenyl)silafluorenyl porphyrin

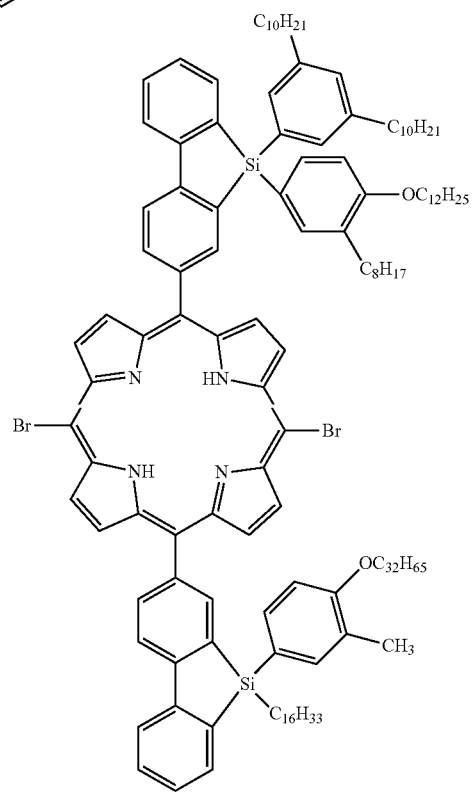

setting up the anhydrous and oxygen-free reactor, weighing 549'-cetyl-9'-(3"-methyl-4"-dotriacontyloxy)phenyl)silafluorenyl-15-(9'-(3",5"-didecyl)phenyl-9'-(3"-octyl-4"-dodecyloxy)phenyl)silafluorenyl porphyrin (0.44 g, 0.2 mmol) and dissolving in 80 mL of orthodichlorobenzene, adding 1 mL of pyridine, cooling the reactants to 0° C., adding N-bromobutanimide (0.07 g, 0.4 mmol), stirring for 0.5 h, after that, the mixture is warmed up to 120° C., then continue to stir for 1 h, adding 5 mL of acetone to terminate the reaction, removing solvent, recrystallizing with diethyl ether/methanol to obtain product, the yield is 85%.

GC-MS (EI-m/z): 2337($M^+$)

fourthly, synthesis of 5,15-dibromo-10-(9'-cetyl-9'-(3"-methyl-4"-dotriacontyloxy)phenyl)silafluorenyl-20-(9'-(3",5"-didecyl)phenyl-9'-(3"-octyl-4"-dodecyloxy)phenyl)silafluorenyl tinporphyrin in the $N_2$ environment, weighing the intermediate 5,15-dibromo-10-(9'-cetyl-9'-(3"-methyl-4"-dotriacontyloxy) phenyl)silafluorenyl-20-(9'-(3",5"-didecyl)phenyl-9'-(3"-octyl-4"-dodecyloxy)phenyl)silafluorenyl porphyrin (0.47 g, 0.2 mmol) and dissolving in 50 mL of dichloromethane, adding ethanol solution (5 ml) containing $SnCl_2$ (0.11 g, 0.6 mmol), stirring at room temperature for 24 h, rotary-evaporating solvent, then eluting on silica gel with dichloromethane/petroleum ether (1/1), collecting and rotary-evaporating solvent to obtain product, the yield is 95%.

GC-MS (EI-m/z): 2451($M^+$)

fifthly, synthesis of 10-(9'-cetyl-9'-(3"-methyl-4"-dotriacontyloxy)phenyl)silafluorenyl-20-(9'-(3",5"-didecyl)phenyl-9'-(3"-octyl-4"-dodecyloxy)phenyl)silafluorenyl tinporphyrin-benzene organic semiconductor material (n=10)

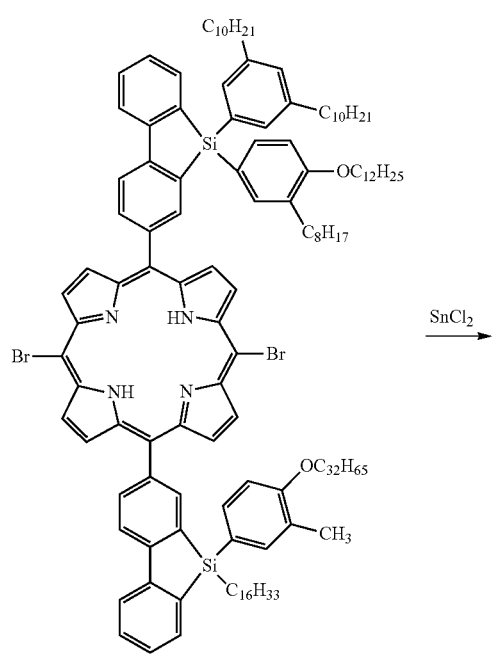

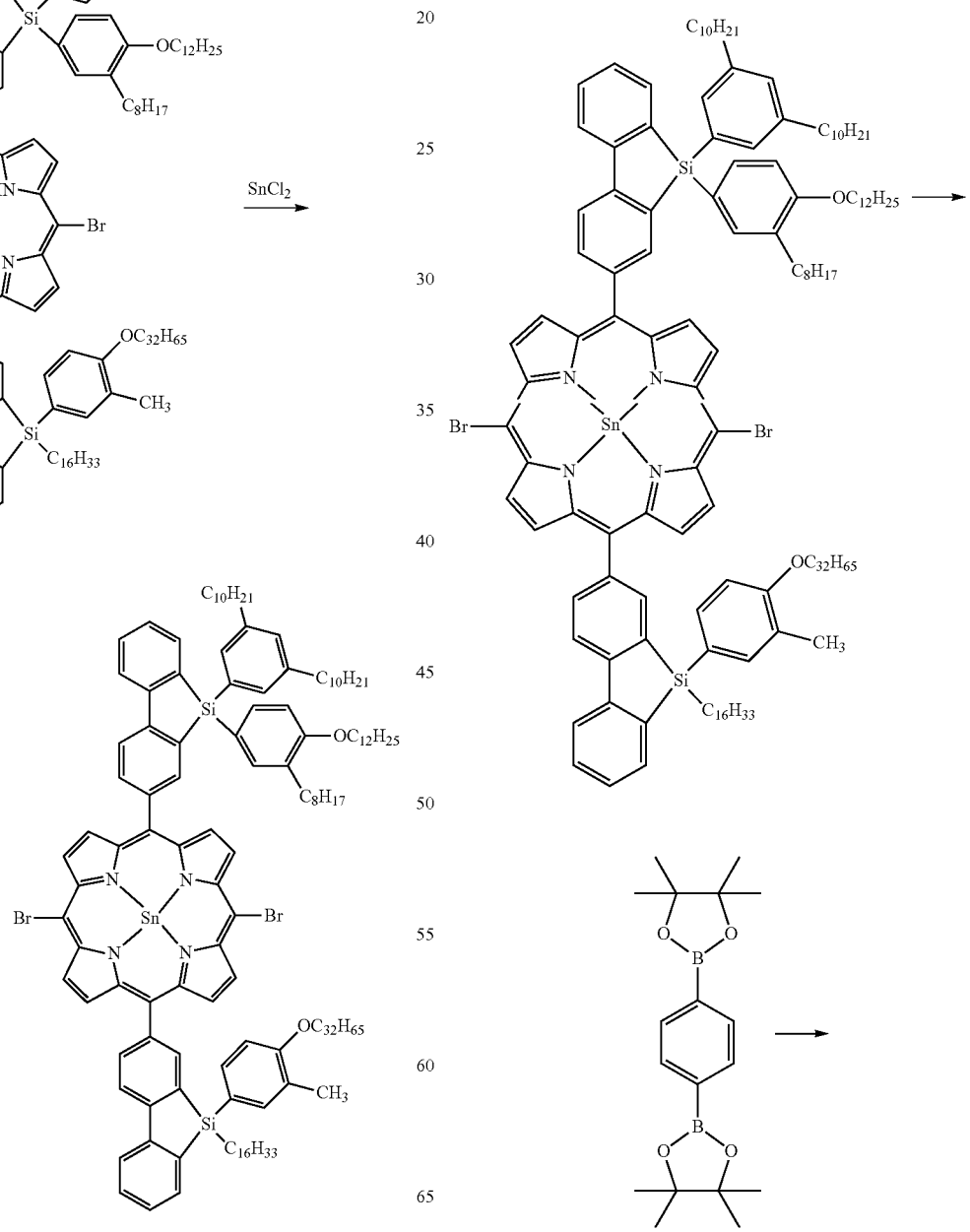

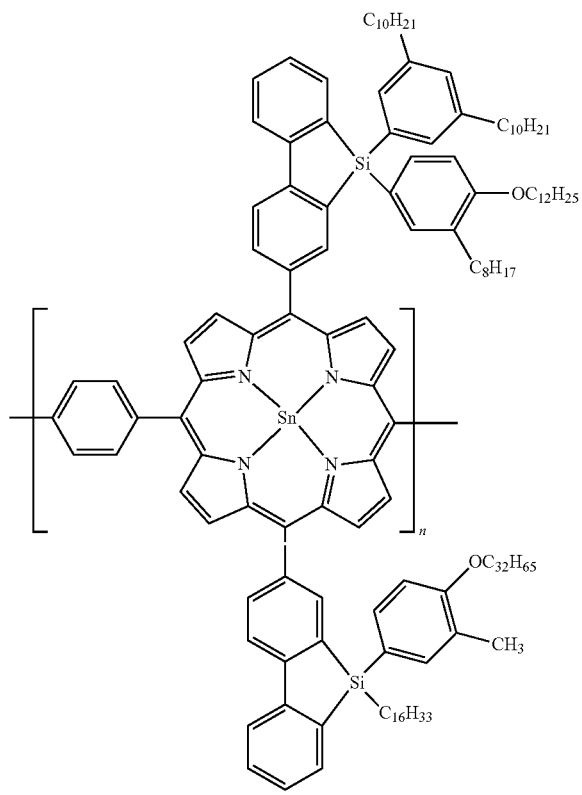

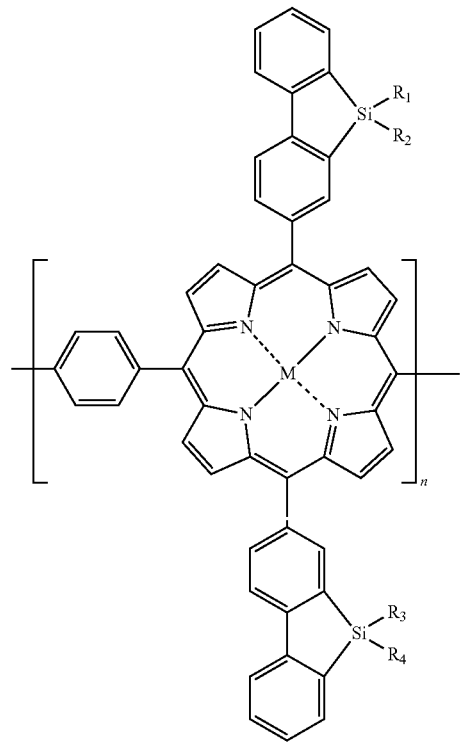

(where n is an integer between 1 and 100, $R_1$, $R_2$, $R_3$, $R_4$ are H, alkyl with $C_1$-$C_{32}$, phenyl, alkyl phenyl or alkoxyl phenyl containing one or more $C_1$-$C_{32}$; M is metal ion) in the field of organic solar cells, organic light-emitting devices, organic field effect transistors, organic optical storages, organic non-linear devices, organic laser devices and others.

The following embodiments are uses of silafluorenyl metalloporphyrin-benzene organic semiconductor material in the field of organic solar cells, organic field effect transistors, and organic light-emitting devices.

EXAMPLE 7

Organic solar cell device using silafluorenyl metalloporphyrin-benzene organic semiconductor material of Example 1 as active layer material An organic solar cell device having the structure diagram shown in FIG. 1. Herein, ITO glass is employed as substrate of the present embodiment, using glass as substrate material, ITO as conducting layer.

The structure of said organic solar cell device is: glass 11/ITO layer 12/PEDOT:PSS layer 13/active layer 14/Al layer 15; herein, the material of active layer is mixture including electron donor material, PCBM which is electron acceptor material; the electron donor material is silafluorenyl metalloporphyrin-benzene organic semiconductor material of the Example 1, electron acceptor material is [6,6]-phenyl C61 butyric acid methyl ester (abbr. PCBM); ITO is indium tin oxide having square resistance of 10-20Ω/□, PEDOT is poly(3,4-ethylenedioxythiophene), PSS is poly(styrenesulfonate); ITO having square resistance of 18Ω/□ is preferred.

The process of preparing said organic solar cell device comprises:

depositing an indium tin oxide (ITO) layer 12 having square resistance of 10-20Ω/□ on one surface of the glass substrate 11 to form conducting layer used as anode, thickness is about 50~300 nm;

under the protection of nitrogen, adding 1,4-bis(4,4,5,5-tetramethyl-1,3,2-dioxaborolan)benzene (66 mg, 0.2 mmol), 5,15-dibromo-10-(9'-cetyl-9'-(3"-methyl-4"-dotriacontyloxy)phenyl)silafluorenyl-20-(9'-(3",5"-didecyl)phenyl-9'-(3"-octyl-4"-dodecyloxy)phenyl)silafluorenyl tinporphyrin (490 mg, 0.2 mmol) and 80 mL of glycol dimethyl ether solvent, vacuumizing to remove oxygen and supplying nitrogen, then adding 10 mg of Pd(PPh$_3$)$_4$ and 4 mL of K$_2$CO$_3$ (5%) solution, heating to 80° C. and reacting for 24 h to obtain mixed solution of reactants of silafluorenyl tinporphyrin-benzene organic semiconductor material.

cooling to room temperature, then dripping the mixed solution into 250 mL of methanol to settle, filtering, washing with methanol, drying; then dissolving with methylbenzene, adding into aqueous solution of sodium diethyldithiocarbamate, then heating the mixed solution to 80° C. and stirring overnight, organic phase is subjected to column chromatography on alumina eluting with chlorobenzene; removing the organic solvent under reduced pressure, settling with methanol, filtering, extracting the obtained solid with acetone in Soxhlet extractor for three days; settling with methanol, filtering, pumping overnight with vacuum pump to obtain silafluorenyl tinporphyrin-benzene organic semiconductor material as a solid product, the yield is 72%. Molecular weight (GPC, THF, R. I): Mn is 23700, Mw/Mn is 2.86.

The present invention also provides uses of silafluorenyl metalloporphyrin-benzene organic semiconductor material having the structure formula of after cleaning the ITO glass with sonicator and treating with oxygen-plasma, coating PEDOT:PSS layer 13 for modification, thickness is in the range of 20 to 300 nm;

coating a active layer 14 on poly(3,4-ethylenedioxythiophene):poly(styrenesulfonate) layer by spin-coating technique, thickness is in the range of 50 to 300 nm, the material of active layer is mixture of silafluorenyl metalloporphyrin-benzene organic semiconductor material of Example 1 and [6,6]-phenyl C61 butyric acid methyl ester (abbr. PCBM);

vacuum evaporating metal aluminium on the surface of active layer to form metal aluminium layer 15 used as cathode, obtaining organic solar cell device;

sealing the organic solar cell device with epoxy resin, then placing it under a airtight condition at 110° C. to anneal for 1.5 h, then cooling to room temperature. Because the chemical structure of the material gets more regular and orderly after annealing, so that the transporting speed and efficiency of carrier are improved, resulting in the improvement of photoelectric conversion efficiency of the device.

Preferably, the thickness of ITO, PEDOT:PSS layer, active layer, Al layer is 150 nm, 50 nm, 120 nm, 100 nm, respectively.

EXAMPLE 8

Organic light-emitting device using silafluorenyl metalloporphyrin-benzene organic semiconductor material of Example 1

Figure 2:
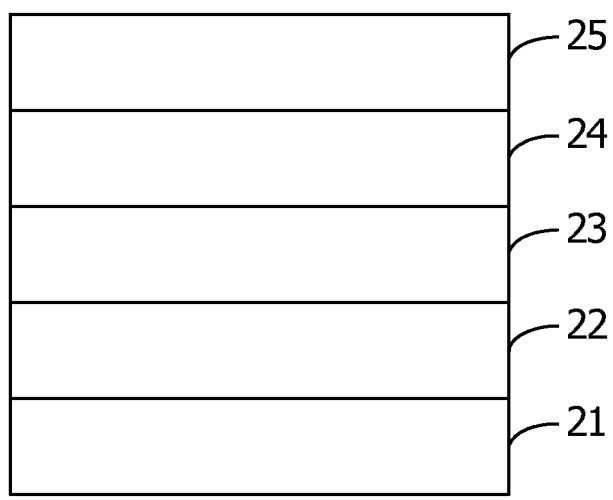
FIG. 2 is a structure diagram of organic light-emitting device using organic semiconductor material of the present invention as luminescent layer.

An organic light-emitting device having the structure diagram shown in FIG. 2. Herein, ITO glass is employed as substrate of the present embodiment, using glass as substrate material, ITO as conducting layer.

The structure of said organic light emitting device is: glass 21/ITO layer 22/luminescent layer 23/LiF buffer layer 24/Al layer 25; herein: the material of luminescent layer is silafluorenyl metalloporphyrin-benzene organic semiconductor material of Example 1.

The process of preparing said organic light-emitting device comprises:

depositing an indium tin oxide (ITO) layer 22 having square resistance of 10-20Ω/□ on one surface of the glass substrate 21 to form conducting layer used as anode, thickness is in the range of 50 to 300 nm; ITO having square resistance of 10Ω/□ is preferred;

producing a luminescent layer 23 using silafluorenyl metalloporphyrin-benzene organic semiconductor material of Example 1 on the surface of ITO by spin-coating technique, thickness is in the range of about 50 to 300 nm;

vacuum evaporating LiF on luminescent layer as buffer layer 14, thickness is in the range of about 0.3 to 2 nm;

vacuum evaporating metal aluminium on said luminescent layer to form metal aluminium layer 25 used as cathode, obtaining said organic light-emitting device.

EXAMPLE 9

Organic field effect transistor using silafluorenyl metalloporphyrin-benzene organic semiconductor material of Example 1

Figure 3:
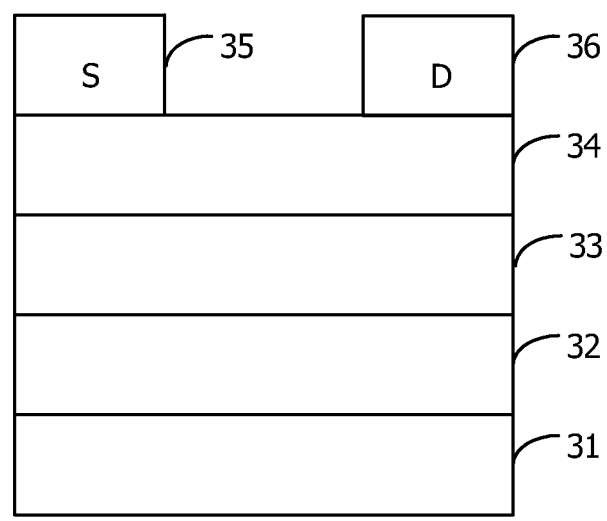
FIG. 3 is a structure diagram of organic field effect transistor device using organic semiconductor material of the present invention as organic semiconductor layer.

An organic field effect transistor having the structure diagram shown in FIG. 3. Herein, doped silica wafer (Si) is employed as substrate of the present embodiment.

The structure of said organic field effect transistor is: Si 31/SiO₂ insulating layer of 450 nm thick 32/octadecyltrichlorosilane (OTS) layer used to modify SiO₂33/organic semiconductor layer 34/source electrode (S) 35 using gold as its material and drain electrode (D) 36; herein: material of organic semiconductor is silafluorenyl metalloporphyrin-benzene organic semiconductor material of Example 1; herein, material of source electrode (S) and drain electrode (D) can also be copper.

The process of preparing said organic field effect transistor comprises:

first, coating a SiO₂ insulating layer of 450 nm thick 32 on a cleaned doped silica wafer 31; next, coating a octadecyltrichlorosilane layer 33 for modification on said SiO₂ insulating layer, thickness is in the range of 10 to 200 nm; then spin-coating a organic semiconductor layer 34 using silafluorenyl metalloporphyrin-benzene organic semiconductor material of Example 1 on said octadecyltrichlorosilane layer, thickness is in the range of about 30 to 300 nm; at last, setting source electrode (S) 35 using gold but not limited to gold and drain electrode (D) 36 spaced apart from each other on said organic semiconductor layer to obtain said organic field effect transistor.

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

What is claimed is:

1. A silafluorenyl metalloporphyrin- benzene organic semiconductor material having the following structure formula (I):

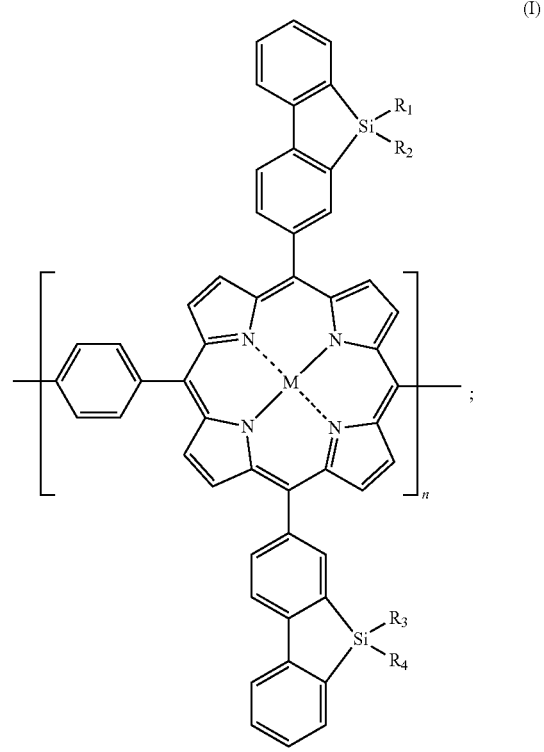

where n is an integer between 1 and 100, $R_1$, $R_2$, $R_3$, $R_4$ are H, alkyl group selected from $C_1$-$C_{32}$, phenyl, alkyl phenyl or alkoxyl phenyl further substituted with one or more arbitrary $C_1$-$C_{32}$ groups; M is metal ion.

2. The silafluorenyl metalloporphyrin- benzene organic semiconductor material according to claim 1, wherein said metal ion is $Zn^{2+}$, $Cu^{2+}$, $Fe^{2+}$, $Co^{2+}$, $Cd^{2+}$, $Pt^{2+}$, $Zr^{2+}$, $Mn^{2+}$, $Ni^{2+}$, $Pb^{2+}$ or $Sn^{2+}$.

3. A preparing method of silafluorenyl metalloporphyrin-benzene organic semiconductor material, comprising:

step S1, in the presence of oxidant and a first catalyst, dissolving dipyrromethane having the structure formula of

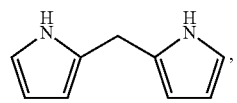 [SMILES: c1c[nH]c(Cc2ccc[nH]2)c1]

a first silafluorene derivative having the structure formula of

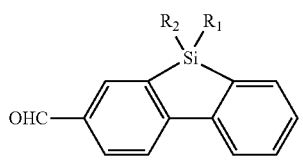

and a second silafluorene derivative having the structure formula of

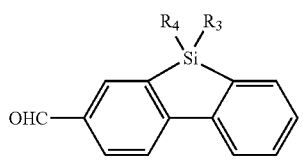

in a first organic solvent, reacting at the temperature of 20° C. to 100° C. for 1 h to 24 h to obtain silafluorenyl porphyrin derivative having the structure formula of

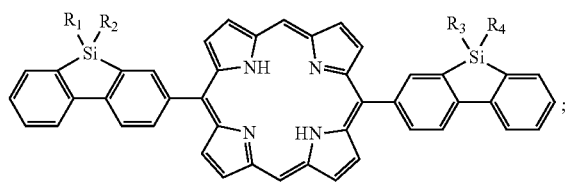

wherein, $R_1$, $R_2$, $R_3$, $R_4$ are H, alkyl group selected from $C_1$-$C_{32}$, phenyl, alkyl phenyl or alkoxyl phenyl further substituted with one or more arbitrary $C_1$-$C_{32}$ groups;

step S2, adding the silafluorenyl porphyrin derivative obtained from step S1 and brominating agent into a second organic solvent, reacting at the temperature of 0° C. to 120° C. for 1 h to 72 h to obtain dibromo-silafluorenyl porphyrin derivative having the structure formula of

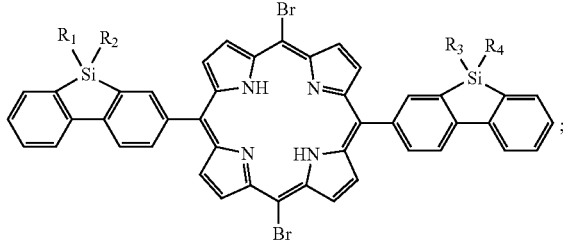

step S3, dissolving the dibromo-silafluorenyl porphyrin derivative obtained from step S2 in a third organic solvent, then adding solution containing M metal ion, stirring at the temperature of 0° C. to 30° C. for 0.5 h to 24 h to obtain dibromo-silafluorenyl metalloporphyrin derivative having the structure formula of

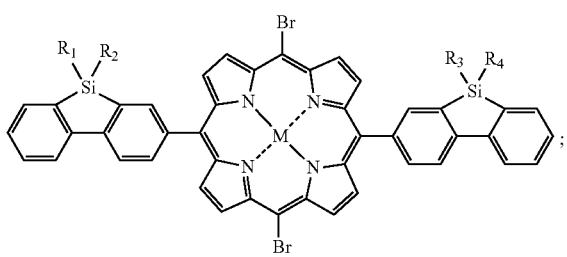

step S4, in the oxygen-free environment, in the presence of a second catalyst and a fourth organic solvent, according to the molar ratio of 1:2 to 2:1, carrying out Suzuki coupling reaction between dibromo-silafluorenyl metalloporphyrin derivative obtained from step S3 and 1,4-p-bis(4,4,5,5-tetramethyl-1,3,2-dioxaborolan) benzene having the structure formula of

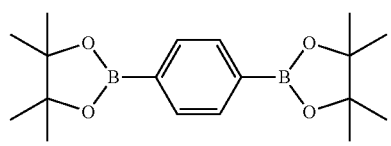

at 50° C. to 120° C. for 12 h to 72 h to obtain said silafluorenyl metalloporphyrin- benzene organic semiconductor material having the structure formula of

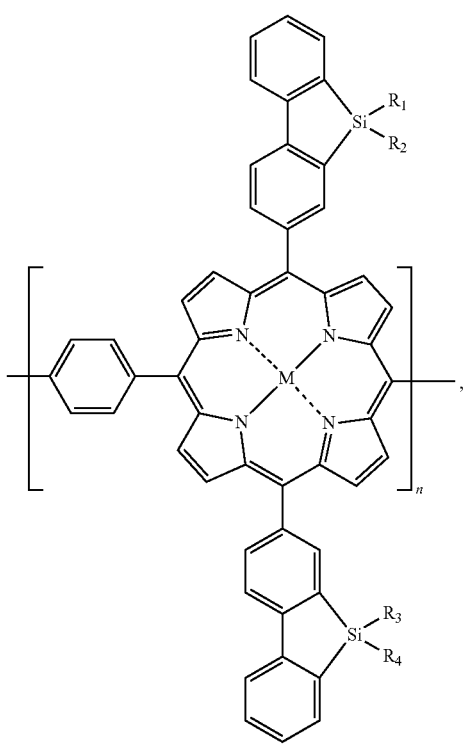

where n is an integer between 1 and 100.

4. The preparing method according to claim 3, wherein, in said step S1, molar ratio of said dipyrromethane, the first silafluorene derivative and the second silafluorene derivative is a:(b+c)=1:1, where a≥b>0, and c≥0; said first catalyst is propionic acid, trifluoroacetic acid; said oxidant is 2,3-dichloro-5,6-dicyano-1,4-benzoquinone; said first organic solvent is selected from trichloromethane, dichloromethane and mixtures thereof.

5. The preparing method according to claim 3, wherein, in said step S2, the molar ratio of used said silafluorenyl porphyrin derivative to used said brominating agent is in the range of 1:2 to 1:5; said brominating agent is N-bromobutanimide; said second organic solvent is at least one of tetrahydrofuran, chloroform, dimethylformamide and orthodichlorobenzene.

6. The preparing method according to claim 3, wherein, in said step S3, molar ratio of said dibromo-silafluorenyl metalloporphyrin derivative to M ion is in the range of 1:1 to 1:5; said third organic solvent is at least one of trichloromethane, tetrahydrofuran, benzene, methylbenzene and dichloromethane; in said solution containing M metal ion, M metal ion is one of $Zn^{2+}$, $Cu^{2+}$, $Fe^{2+}$, $Co^{2+}$, $Cd^{2+}$, $Pt^{2+}$, $Zr^{2+}$, $Mn^{2+}$, $Ni^{2+}$, $Pb^{2+}$ and $Sn^{2+}$, solvent which makes the solution containing M is at least one of methanol, ethanol and water.

7. The preparing method according to claim 3, wherein, in said step S4, said second catalyst is organopalladium or mixture of organopalladium and organic phosphine ligand;
said organopalladium is $Pd_2(dba)_3$, $Pd(PPh_3)_4$, $Pd(OAc)_2$ or $Pd(PPh_3)_2Cl_{12}$;
said organic phosphine ligand is $P(o\text{-}Tol)_3$ or tricyclohexyl phosphine;
said fourth organic solvent is at least one of tetrahydrofuran, dichloromethane, chloroform, dioxane, dimethylformamide, glycol dimethyl ether, dimethyl sulfoxide, benzene, chlorobenzene and methylbenzene.

8. The preparing method according to claim 3, wherein, said step S4 further comprises preparation of 1,4-p-bis(4,4,5,5-tetramethyl-1,3,2-dioxaborolan) benzene comprising:
adding p-dibromobenzene having the structure formula of

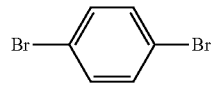

into a fifth organic solvent, cooling to −78° C. with liquid nitrogen/ isopropanol, then dripping n-butyl lithium and reacting at −78° C. for 1 h to 3 h, after that, adding 2-isopropoxy-4,4,5,5-tetramethyl-1,3,2-dioxaborolane having the structure formula of

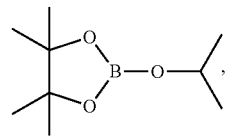

continue to react at −78° C. for 0.5 h to 2 h, then warming naturally to room temperature and reacting for 6 h to 36 h to obtain said 1,4-p-bis(4,4,5,5- tetramethyl-1,3,2-dioxaborolan) benzene.

9. The preparing method according to claim 8, wherein, said fifth organic solvent is at least one of tetrahydrofuran, diethyl ether and dioxane; the molar ratio of said p-dibromobenzene to 2-isopropoxy-4,4,5,5-tetramethyl-1,3,2- dioxaborolane is in the range of 1:2 to 5.

* * * * *